United States Patent
Meloul et al.

(10) Patent No.: US 6,261,219 B1
(45) Date of Patent: Jul. 17, 2001

(54) INTRALUMINAL RADIATION TREATMENT SYSTEM

(75) Inventors: Raphael F. Meloul, Atlanta; Richard A. Hillstead, Duluth; George K. Bonnoitt, Jr., Tucker, all of GA (US); Martin B. Tobias, Westminster, CO (US); David S. Halpern, Alpharetta; Roelof Trip, Lawrenceville, both of GA (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 09/304,752

(22) Filed: May 4, 1999

Related U.S. Application Data

(60) Provisional application No. 60/084,080, filed on May 4, 1998.

(51) Int. Cl.[7] .................................................... A61N 5/00
(52) U.S. Cl. .......................... 600/3; 600/7; 600/4; 600/1
(58) Field of Search .................................. 600/1, 3, 4, 7, 600/8; 604/93, 57, 59, 60, 97, 98, 99, 100

(56) References Cited

U.S. PATENT DOCUMENTS

| | | | | |
|---|---|---|---|---|
| 2,269,963 | * | 1/1942 | Wappler | 600/7 |
| 5,683,345 | * | 11/1997 | Waksman et al. | 600/3 |
| 5,840,008 | * | 11/1998 | Klein et al. | 600/3 |
| 5,863,284 | * | 1/1999 | Klein | 600/3 |
| 5,899,882 | * | 5/1999 | Waksman et al. | 604/96 |
| 6,007,474 | * | 12/1999 | Rydell | 600/7 |
| 6,013,020 | * | 1/2000 | Meloul et al. | 600/7 |

* cited by examiner

*Primary Examiner*—Eric F. Winakur
*Assistant Examiner*—Navin Natnithithadha
(74) *Attorney, Agent, or Firm*—Cook, Alex, McFarron, Manzo, Cummings & Mehler, Ltd.

(57) ABSTRACT

This invention is a transfer device and catheter assembly for the delivery of treatment elements to a selected location within the intraluminal passageways of a patient as part of an intraluminal radiation system. The transfer device includes a gate member that permits the treatment elements to leave the transfer device only if the catheter is attached thereto. A pressure indicator provides a visual indication of the fluid pressure within the transfer device, and a pressure relief valve provides for a release of the fluid if the pressure exceeds a predetermined pressure. Transfer device also includes a treatment element detection system, low power indicator, a counter system, and an electromagnetic locking mechanism to prevent the opening or closing of the gate member when less than all of the treatment elements are in the transfer device.

13 Claims, 25 Drawing Sheets

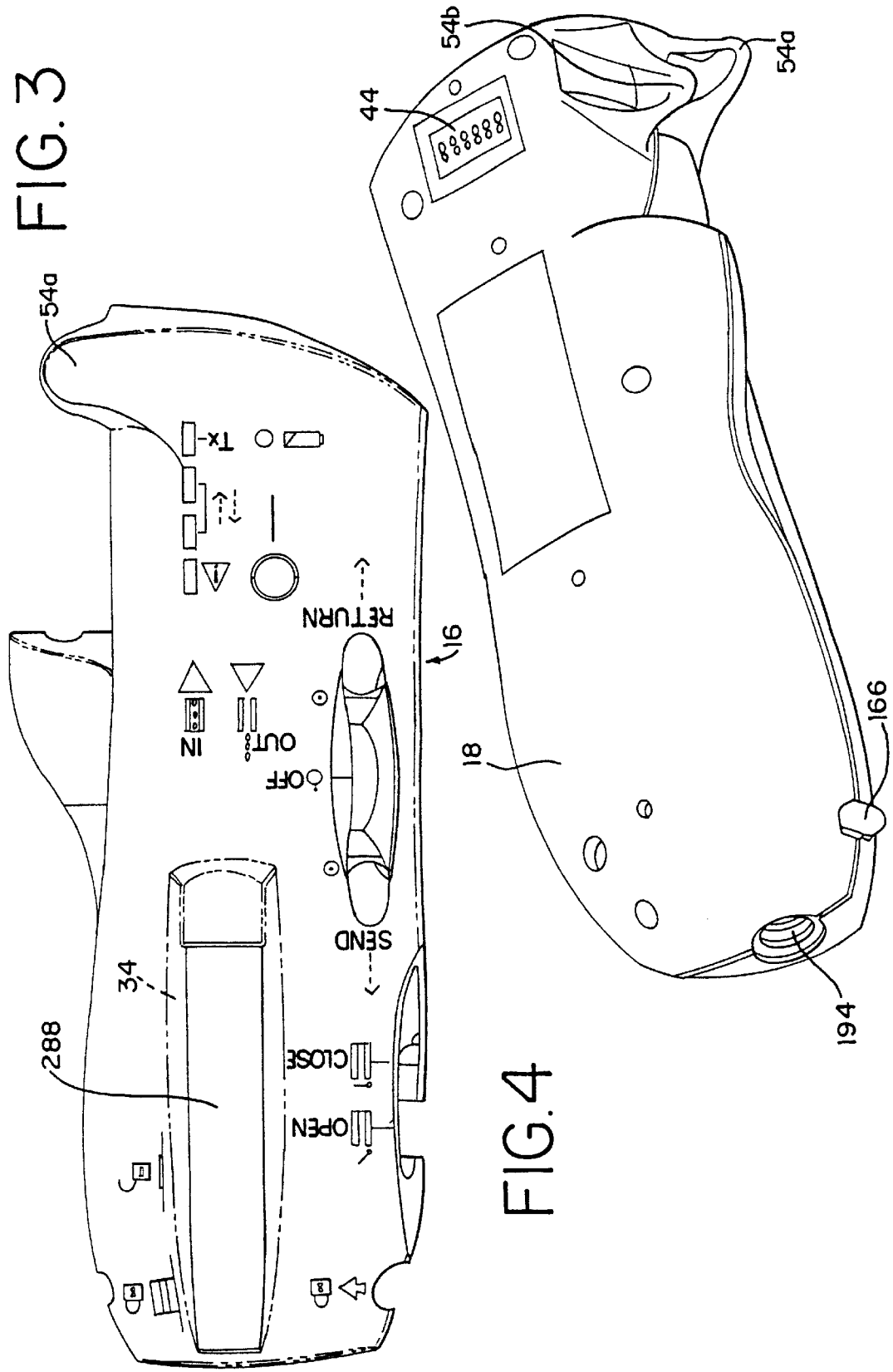

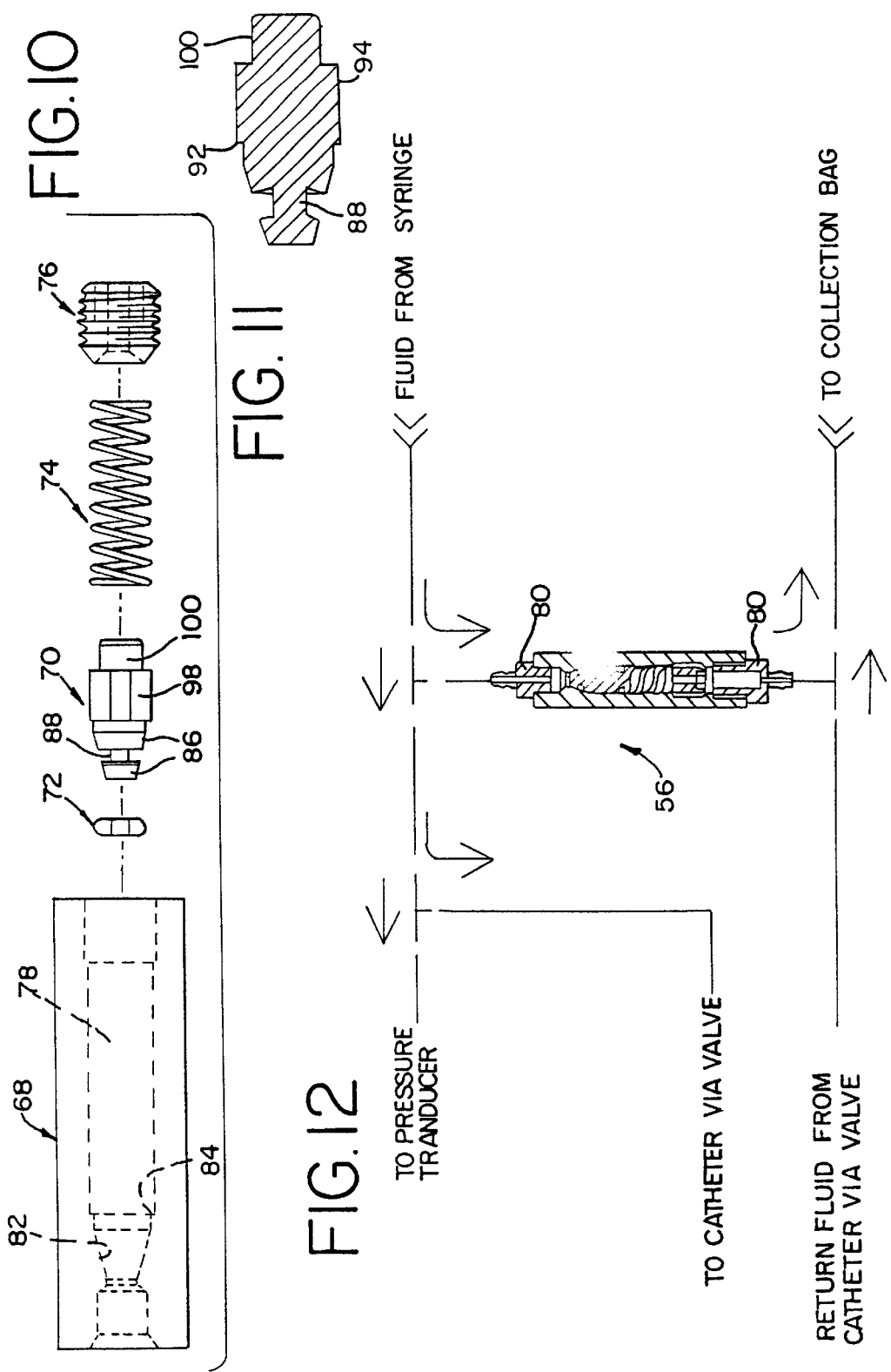

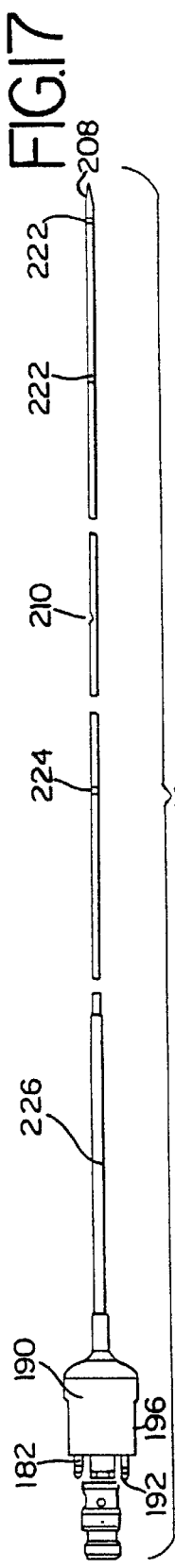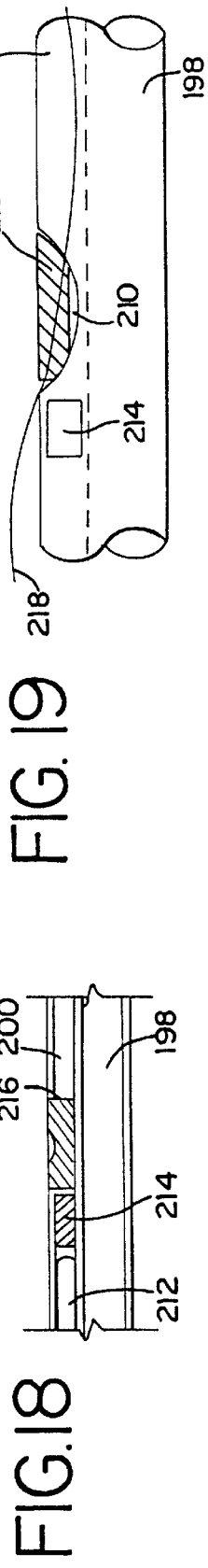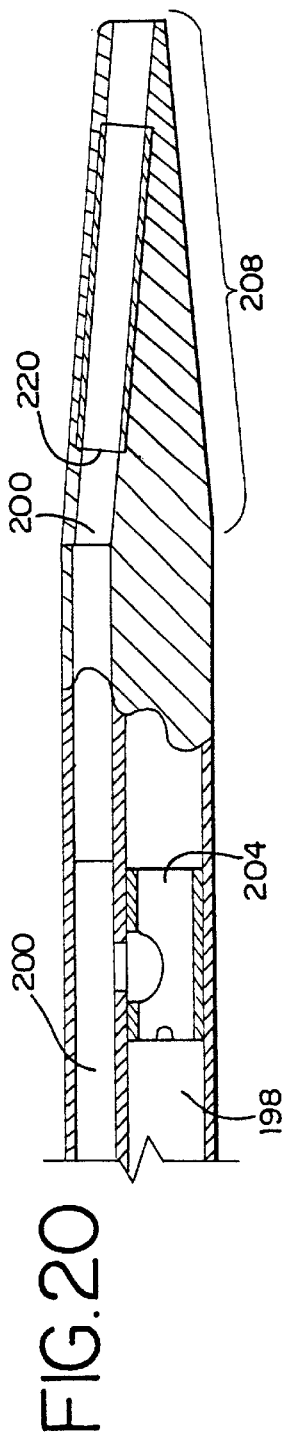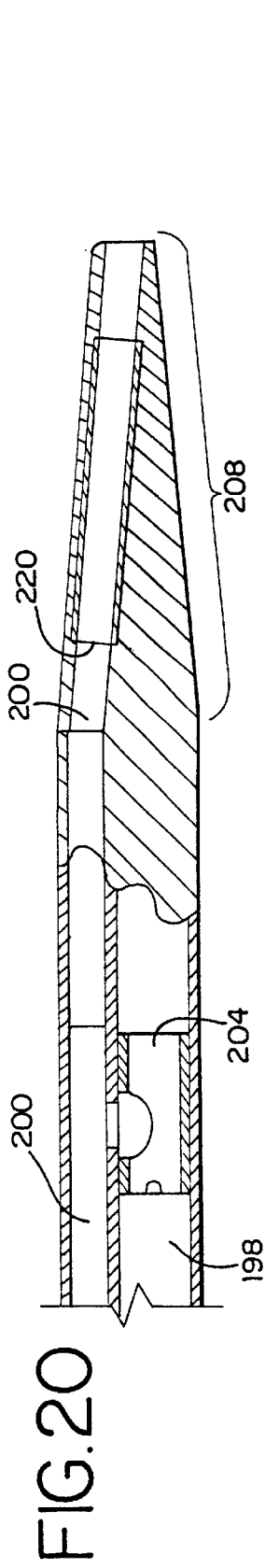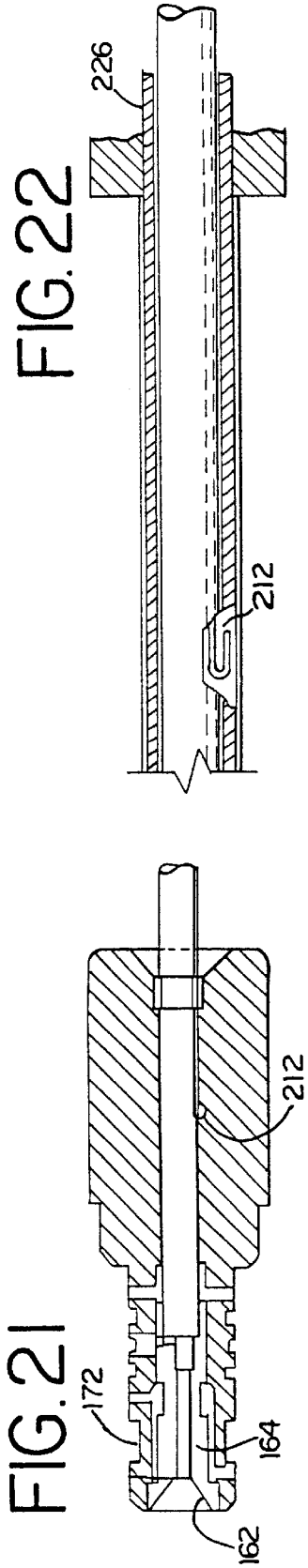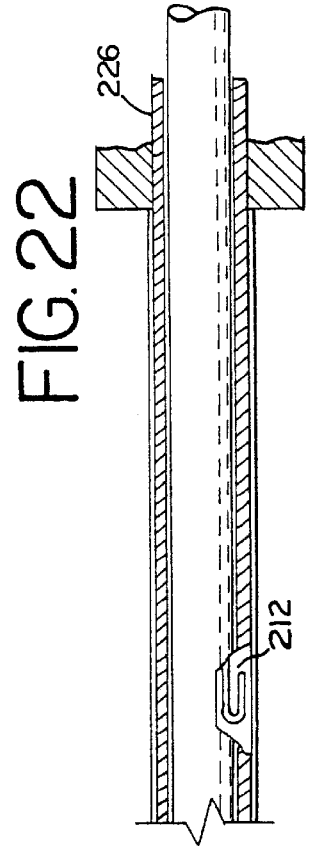

FIG. 31
FIG. 32
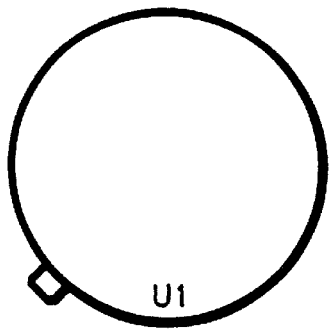
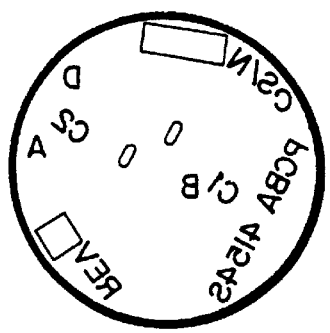
FIG. 33
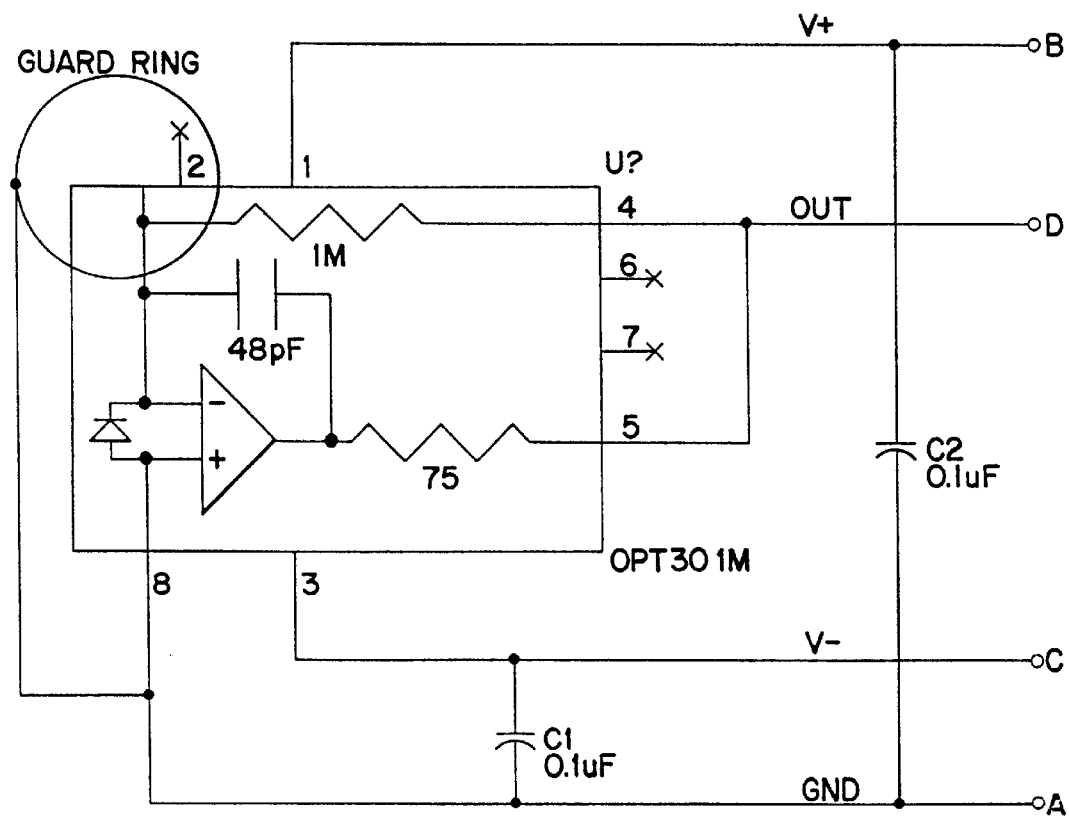

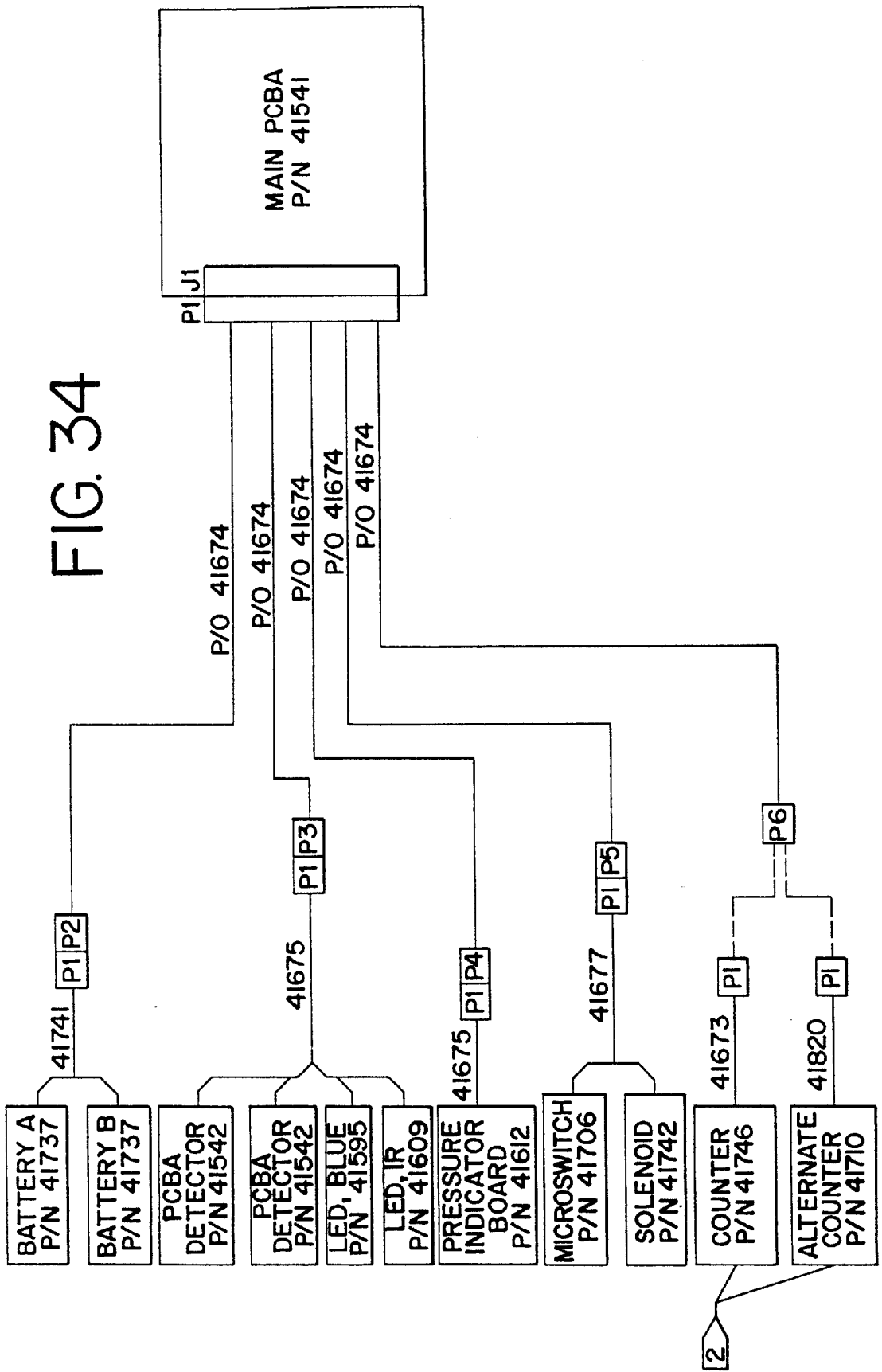

INTRALUMINAL RADIATION TREATMENT SYSTEM

CROSS REFERENCE TO RELATED APPLICATION

This application claims the benefit of U.S. Provisional Application Ser. No. 60/084,080, filed May 4, 1998.

The present invention relates generally to an intraluminal radiation system for the delivery of treatment elements by way of a catheter to a selected location within the intraluminal passageways of a patient. More particularly, the present invention relates primarily to an improved transfer device for handling the treatment elements and delivering them to the catheter and an improved catheter assembly.

BACKGROUND OF THE INVENTION

Since the late 1970's balloon angioplasty techniques have become widely used for opening blockages in coronary arteries. Briefly, the enlargement of the artery is achieved by advancing a balloon catheter into a narrowed portion of the artery and inflating the balloon to expand the diameter of the artery, thus opening the artery for greater blood flow. Atherectomy techniques, in which blockages are removed or reduced in size, have also been used to the same end.

While balloon angioplasty has proved an effective way of opening the coronary arteries, in a significant number of cases the arteries will narrow again at the location where the balloon was expanded, such narrowing being termed restenosis. Restenosis is believed to be caused by formation of scar tissue at the site of the angioplasty that results from the injury to the artery caused by the inflation of the balloon. More recently, intraluminal radiation has been used after angioplasty or atherectomy to treat the affected area of the artery to inhibit cell proliferation and wound healing response and, consequently, help to prevent restenosis. Methods and apparatus for such intraluminal radiation treatment are disclosed in the co-pending applications, Ser. No. 08/628,231, filed Apr. 4, 1996, now U.S. Pat. No. 5,899,882 and Ser. No. 08/936,058, filed Sep. 23, 1997, now U.S. Pat. No. 6,013,020, both of which are incorporated herein by reference. These applications generally disclose an apparatus comprising a catheter, which is inserted intraluminally into the patient and advanced to the site of the area to be treated, and a transfer device for facilitating either the hydraulic or pneumatic advancement and retrieval of individual radioactive treating elements or "seeds" along the catheter to and from the treatment site.

As with any device inserted into the vascular system, it must have sufficient integrity to insure that no pieces or elements are separated from or exit the device into the vascular system. This is particularly true for the treating elements which are moved to and from the distal end of the catheter. Additionally, because the device is intended to use radioactive treating elements, there is a heightened need for safety to prevent any unintended exposure of either the patient or the user to radioactivity.

Use of the apparatus described in the above-identified co-pending application has suggested several areas where the device could be improved to reduce the possibility of having treatment elements escape from the system, thus enhancing patient and user safety.

Consequently, it is the principal object of the present invention to provide a transfer device and catheter assembly that has additional safeguards to protect the patient and user.

More particularly, it is an object of the present invention to provide a transfer device/catheter assembly in which the treatment elements cannot be inadvertently released from the transfer device.

It is a further object to insure that the operator has a visual indication of the magnitude of the hydraulic or pneumatic pressures to which the transfer device/catheter assembly is subjected during the advancement and retrieval of the treating elements and that this pressure does not exceed a predetermined "safe" pressure.

It is an additional object to provide a method and system for detecting the presence or absence of treating elements in the transfer device and for providing a visual indication of such presence or absence of treating elements.

SUMMARY OF THE INVENTION

These objects, and others that will become apparent upon reference to the following detailed description are accomplished in one aspect by an actuator assembly for the transfer device that includes a gate member that is moveable between a first position that prevents treating elements from entering the lumen of the catheter and a second position that permits treating elements to enter the lumen. An electromagnetic interlocking mechanism prevents the gate member from opening or closing when less than all of the treatment elements and marker seeds are within the quartz housing. The interlocking mechanism is controlled by an electronic seed detection system.

In another aspect of the invention, a pressure indicator is provided that includes a transducer, related electronic circuitry, and an indicator light display.

In a further aspect, a pressure relief valve is provided comprising a cylinder that includes an inlet port through which pressurized fluid can enter, the piston being biased. The cylinder includes a portion having a inside diameter greater than that portion of the cylinder in which the piston is disposed and an outlet port in communication with the enlarged-diameter portion of the cylinder. Consequently, when the fluid pressure is sufficient to move the piston into the enlarged-diameter portion of the cylinder, fluid escapes passed the piston and exits the cylinder through the exit port.

In a further aspect of the invention, a method is provided for determining whether the treating elements reside in the transfer device. The method includes encapsulating the treating elements in a material having a known wavelength/reflection ratios; shining to lights of different wavelengths into the area in the transfer device where the treating elements normally reside before and after being introduced into the catheter; measuring the reflectively of the two lights as reflected off the area in the transfer device; determining the wavelength/reflection ratios of the reflected light; comparing the measured wavelength/reflection ratios with the known wavelength/reflection ratios; and indicating whether the measured ratios are substantially the same as the known ratios.

A system for determining whether the treating elements and marker seed reside in the transfer device is another aspect of the invention and includes a power source; a first light source optically connected to the targeted location in the transfer device and that emits a light having a first wavelength; a second light source optically connected to the targeted location that emits light having a second wavelength; a photosensor optically connected to the targeted location that measures the light reflected off the targeted location and creating a signal corresponding thereto; a window detector for determining whether the signal created by photosensor is within a predetermined band corresponding to a signal which would be created by light of first and second wavelengths being reflected off the element; and an indicator light that is activated if the signal created by the photosensor is within the predetermined band.

In another aspect of the invention, the transfer device includes an electronic counter to keep a running total of the number of transfer device uses for radiation treatment. A low-power indicator display may also be included.

BRIEF DESCRIPTION OF THE DRAWINGS

FIG. 3 is a plan view of the transfer device of FIG. 1.

FIG. 4 is a perspective view of the transfer device of FIG. 1 showing the opposite side shown in FIG. 2.

FIG. 10 is an exploded view of a pressure indicator gauge and pressure relief valve of the transfer device of FIG. 1.

FIG. 11 is a cross-sectional view of a component of the pressure indicator gauge and pressure relief valve of FIG. 10.

FIG. 12 is a cross-sectional view of the pressure indicator gauge and pressure relief valve of FIG. 10, with the fluid flow therethrough shown schematically.

FIGS. 17–22 show a catheter and connector for use in the present invention.

FIGS. 31 and 32 are printed circuit boards for the photo detector for the transfer device of FIG. 1.

FIG. 33 is a wiring diagram for the photo detector for the transfer device of FIG. 1.

FIG. 34 is a wiring diagram for the transfer device of FIG. 1.

DETAILED DESCRIPTION OF THE PREFERRED EMBODIMENT

Figures 1, 2:
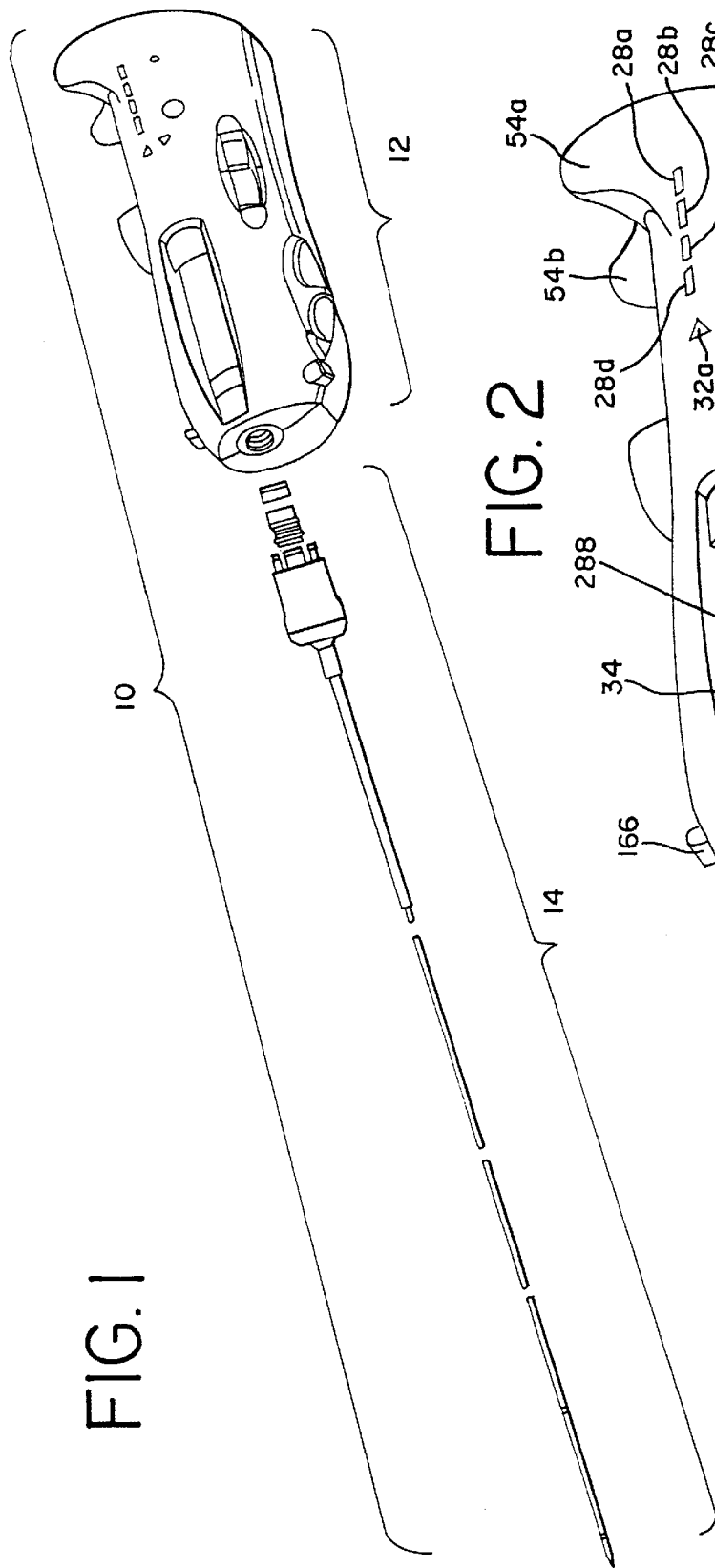
FIG. 1 is a schematic drawing of an embodiment of the intraluminal radiation treatment system of the present invention comprising a transfer device, a delivery catheter and a connector for connecting the two.
FIG. 2 is a perspective view of the transfer device of FIG. 1.

Turning to FIG. 1, there is seen an improved catheter-based radiation delivery system 10 of the present invention. The basic system, its use, and its principles of operation are described in the co-pending U.S. patent applications Ser. No. 08/628,231, filed Apr. 4, 1996, now U.S. Pat. No. 5,899,882, and Ser. No. 08/936,058, filed Sep. 23, 1997, now U.S. Pat. No. 6,013,020 both of which were incorporated by reference above. The system 10 is made up of transfer device 12 and rapid exchange radiation delivery catheter 14.

Turning to FIGS. 2 and 7–9, the transfer device 12 has an ergonomically designed exterior which is easily handled by the user and has internal components which include a pressure indicator, pressure relief valve, flow control valve and pathways, quartz housing, a catheter connector/pin gate interlock system, and a treatment element electronic detection system, all described in greater detail below.

The transfer device 12 of the present invention is a hand holdable device. The transfer device 12 preferably weighs less than two pounds and preferably is sized to be no more than four inches wide, nine inches long, and three inches high.

Figure 5:
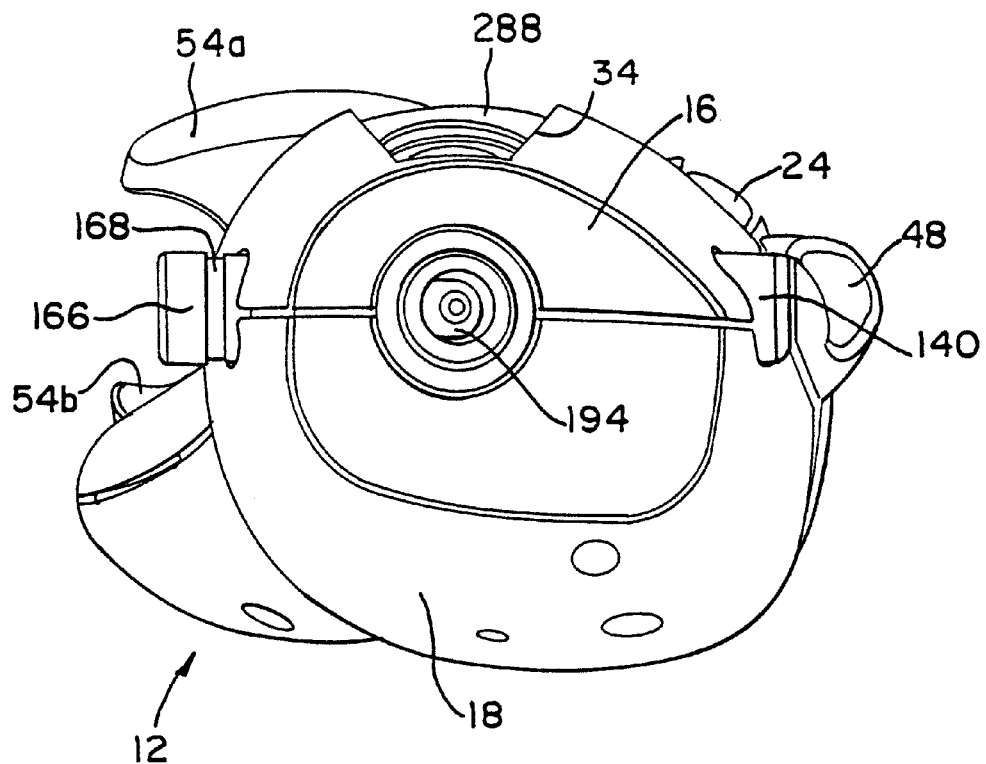
FIG. 5 is an end view of the transfer device of FIG. 1 looking at the proximal end.
Figure 6:
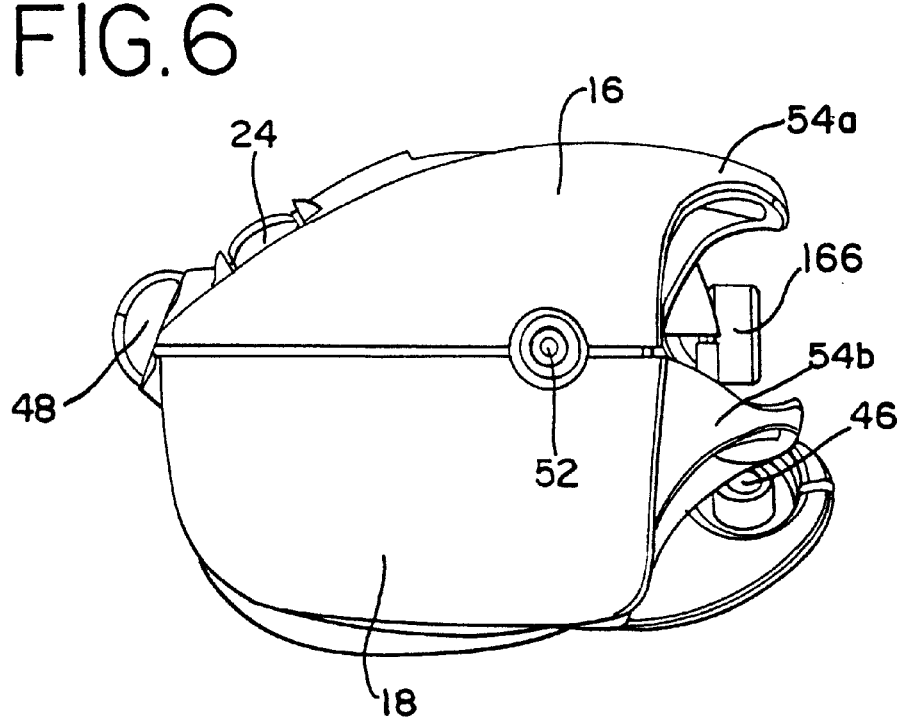
FIG. 6 is an end view of the transfer device of FIG. 1 looking at the distal end.
Figure 7:
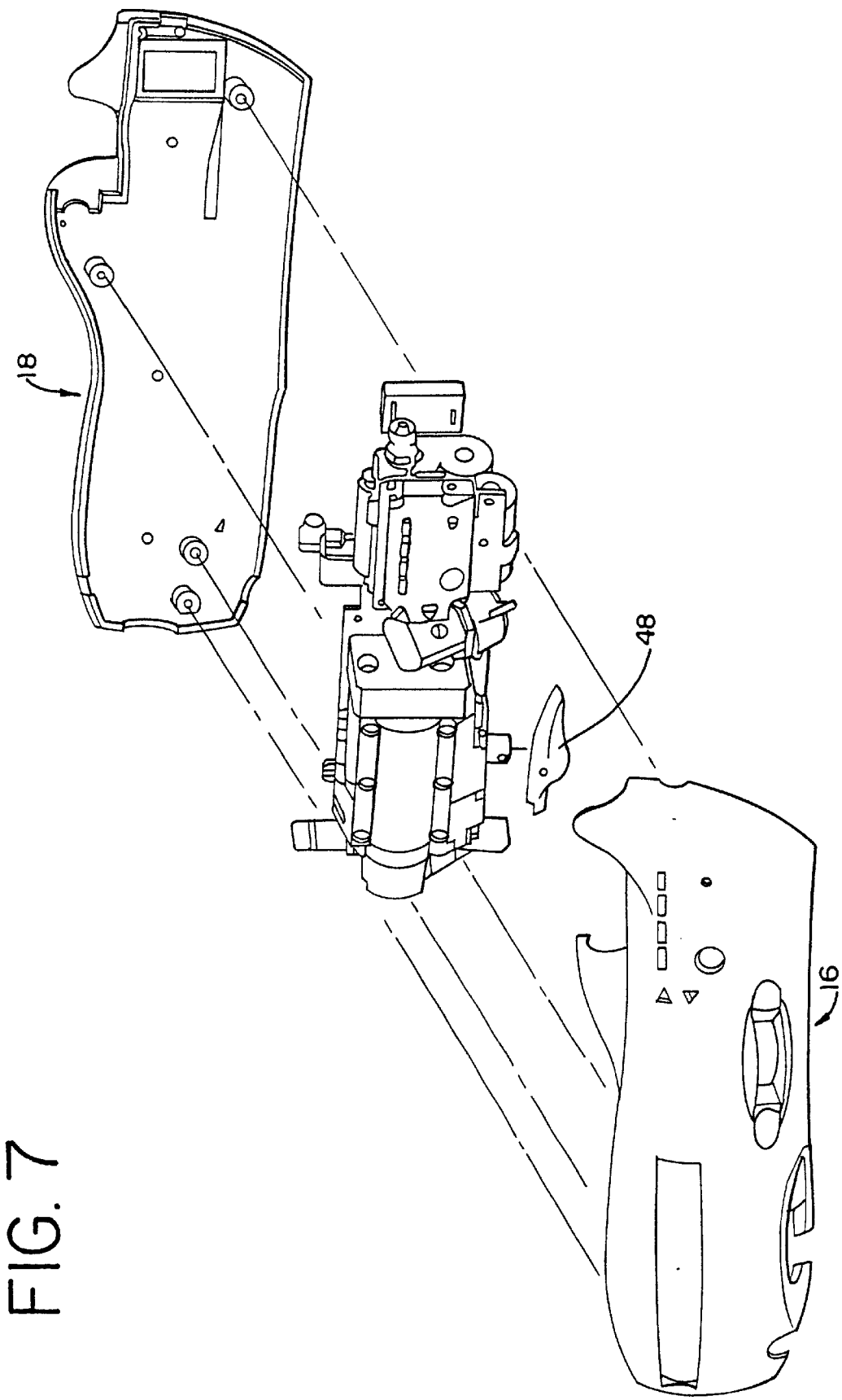
FIG. 7 is an exploded perspective view of the transfer device of FIG. 1.
Figure 8:
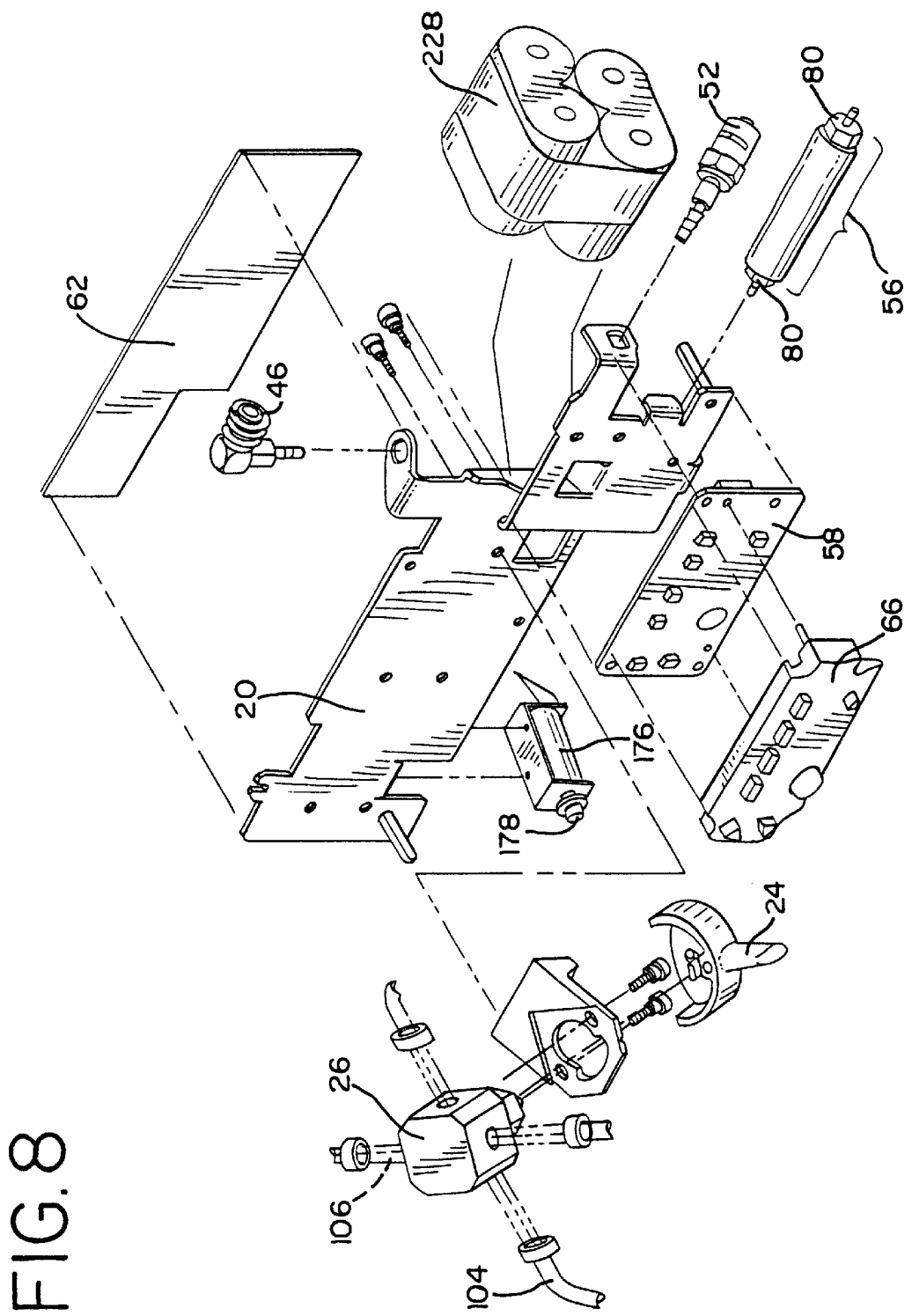
FIG. 8 is an exploded perspective view of selected internal components of the transfer device of FIG. 1.

As seen in the exploded view of FIG. 7, the exterior of the transfer device 12 is made up of an upper portion 16 and a lower portion 18, each portion comprising a shell half. The two shell halves 16, 18 fit together to enclose a chassis 20, on which the components of the transfer device 12 are mounted. Openings in the upper shell half 16 allow user to manipulate a power button 22 for activating the electronics of the device, and a fluid control switch 24 for activating the fluid control valve 26 (FIG. 8). Additional openings in the upper shell half allow the user to see the pressure indicator LEDs (light emitting diodes) 28a–d, low battery indicator LED 30, and the treatment element indicator LEDs 32a–d. The upper shell portion 16 also includes a magnifying window 34 for viewing the quartz sleeve 36, where the treatment elements and marker seeds are stored, and distal passageways (not shown) leading from the quartz sleeve 36 to the distal opening 40 of the transfer device 12. The lower shell portion 18 has a window 42 for viewing the counter display 44 which identifies the number of procedures that have been performed with the transfer device. The mating edges of the two shell halves 16 and 18 together create openings along the sides of the transfer device 12 that allow access to a fluid entry port 46, a sliding gate actuator switch 48 and either end of a latch mechanism for the catheter connector (described in detail below). The mating edges of the two shell halves 16 and 18 also create the opening 40 (FIG. 5) at the distal end of the transfer device 12 for entry of the catheter connector and an opening at the proximal end of the transfer device 12 (FIG. 6) for allowing access to a fluid exit port 52, which preferably extends minimally, if at all, beyond the exterior wall of the transfer device 12. A compartment or clip (neither shown) may be added to the transfer device 12 to store or secure a fluid collection bag (not shown). Polyurethane is an example of a material that can be used to make the two shell halves 16 and 18. Other durable materials can also be used.

Figure 13:
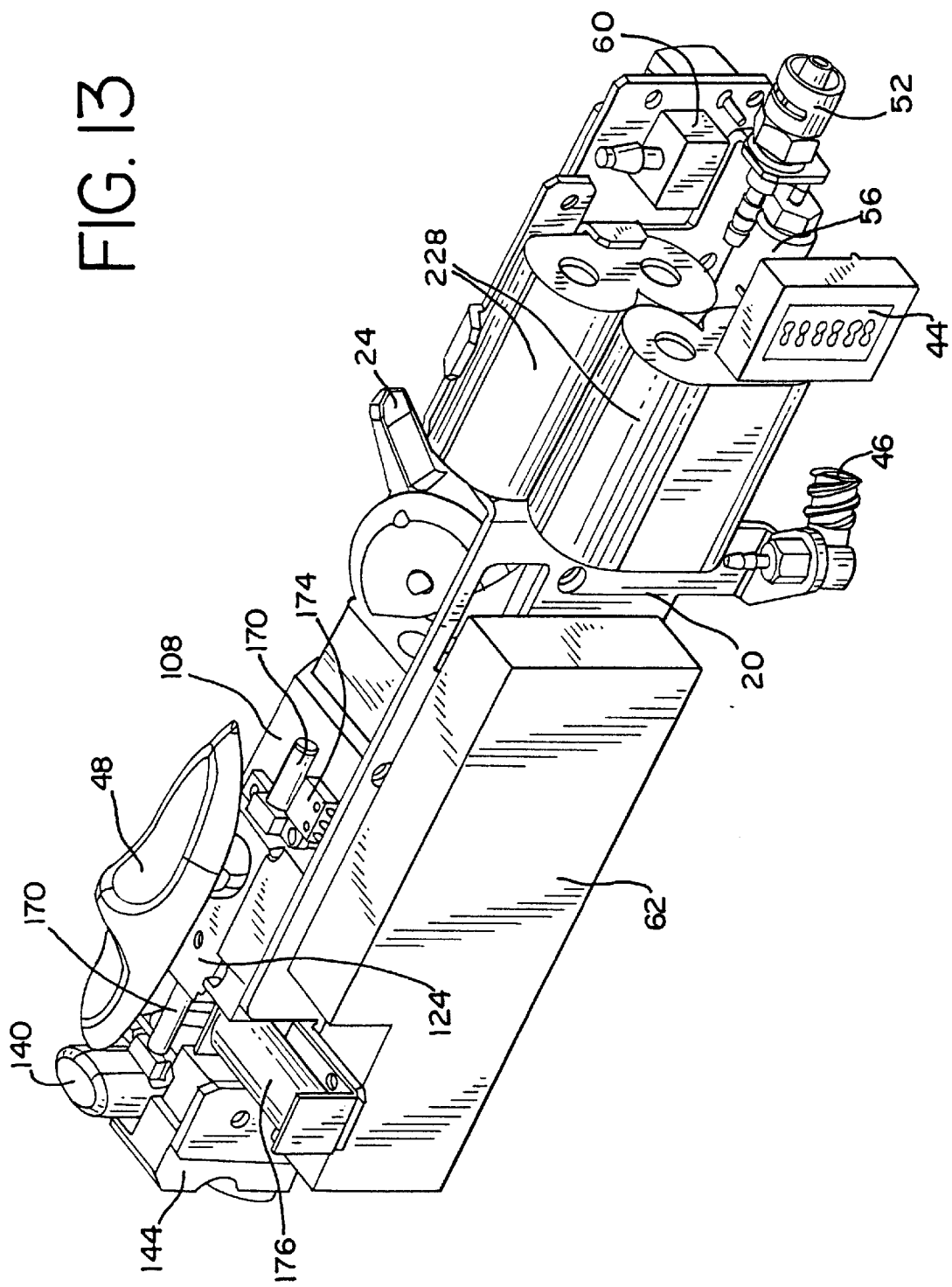
FIG. 13. is a perspective view of selected interior components of the transfer device of FIG. 1 mounted on a chassis.

A source of pressurized fluid (liquid or gas), such as a fluid filled syringe or automatic fluid pump, is connected to fluid entry port 46 for hydraulic or pneumatic delivery and retrieval of treatment elements. The fluid entry port 46 as shown in FIG. 13 has a luer connector. In addition, an extension connector may be connected to the luer connector to more easily couple a syringe or pump to the fluid entry port. Two offset arms 54a and 54b (FIGS. 2–6) extend from the shell portions 16 and 18 to support and orient a syringe along side transfer device 12 at predetermined angles with respect to its longitudinal axis to afford easier manipulation of the syringe plunger and proper alignment between the distal end of the syringe and the fluid entry port 46. The arms 54a, 54b may be designed and positioned to orient a syringe at various angles. One such arrangement may angle the syringe outwardly approximately seven degrees and upwardly approximately twenty-five degrees with respect to the longitudinal plane of the transfer device 12. At least one arm preferably is curved, so as to partially wrap around the attached syringe, to provide for increased support while applying force to the syringe. The support arms 54a and 54b are configured such that the arm 54a extending from the upper shell portion is proximal to the arm 54b of the lower shell portion, thus providing a clearer site line between the proximal end of the transfer device 12 and the fluid entry port 46 for quick and easy connection of the syringe.

With reference to FIGS. 8 and 10–12, the chassis 20 of transfer device 12 also supports a pressure indicator and a pressure relief valve 56 that work independently from one another. The pressure indicator assists the user in determining the appropriate pressures necessary to send and retrieve treatment elements to and from the distal end of the catheter and to maintain the treatment elements at the distal end of the catheter during treatment. The pressure relief valve 56 prevents overpressurization of the system which could damage the catheter 14 and/or the transfer device 12.

Figure 25:
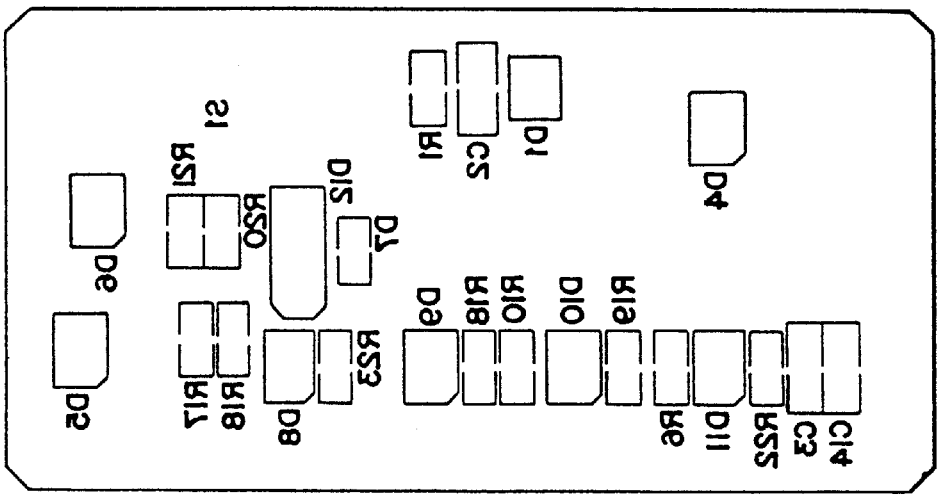
FIGS. 24 and 25 show printed circuit boards for the pressure indicator gauge of FIG. 10.
Figure 24:
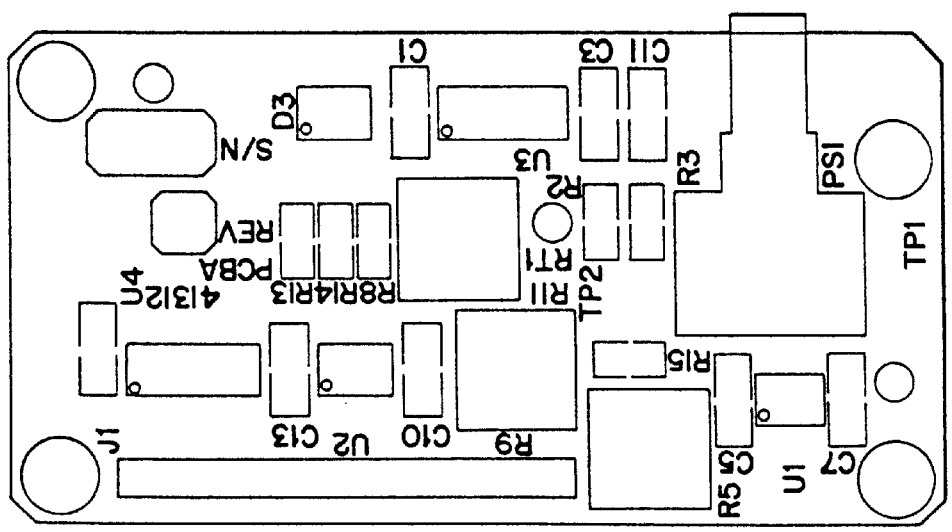
Figure 26A:
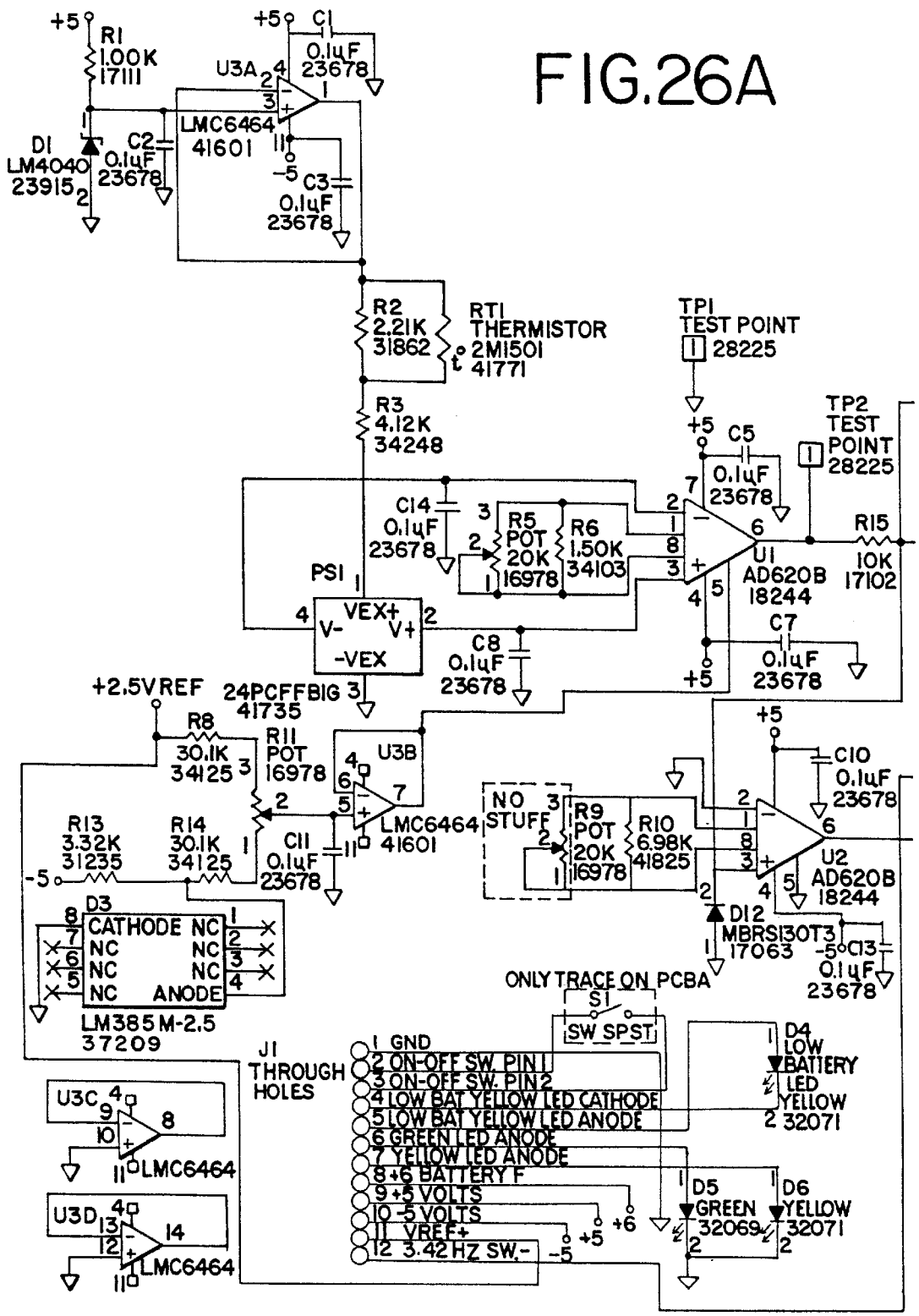
FIGS. 26A and 26B are a circuit diagram for the pressure indicator gauge of FIG. 10.
Figure 26B:
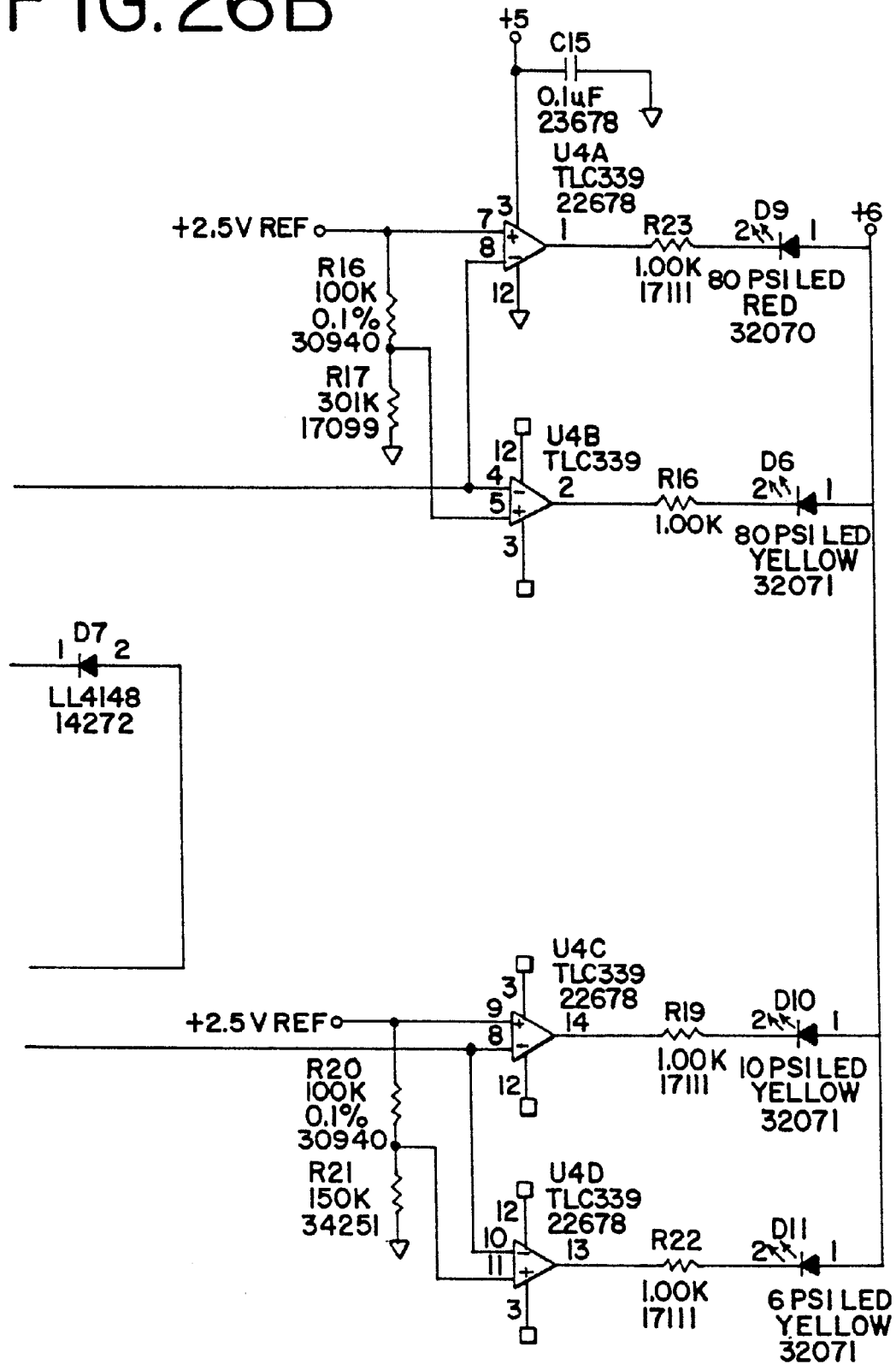
Figure 27:
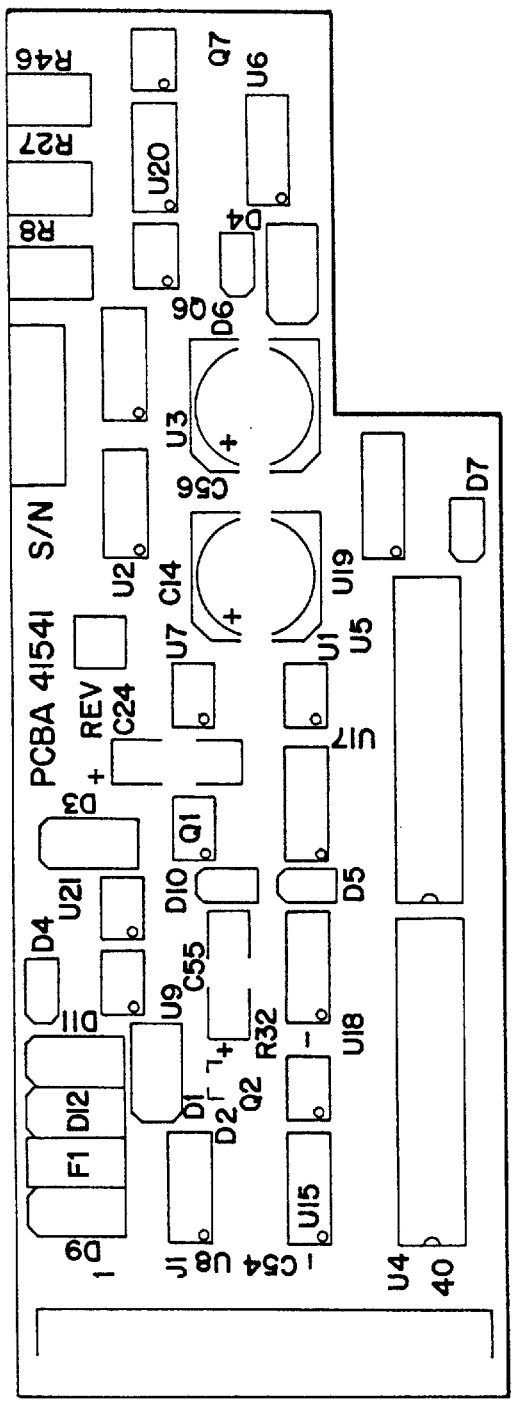
FIGS. 27 and 28 are printed circuit boards for the main pc board for the transfer device of FIG. 1.
Figure 28:
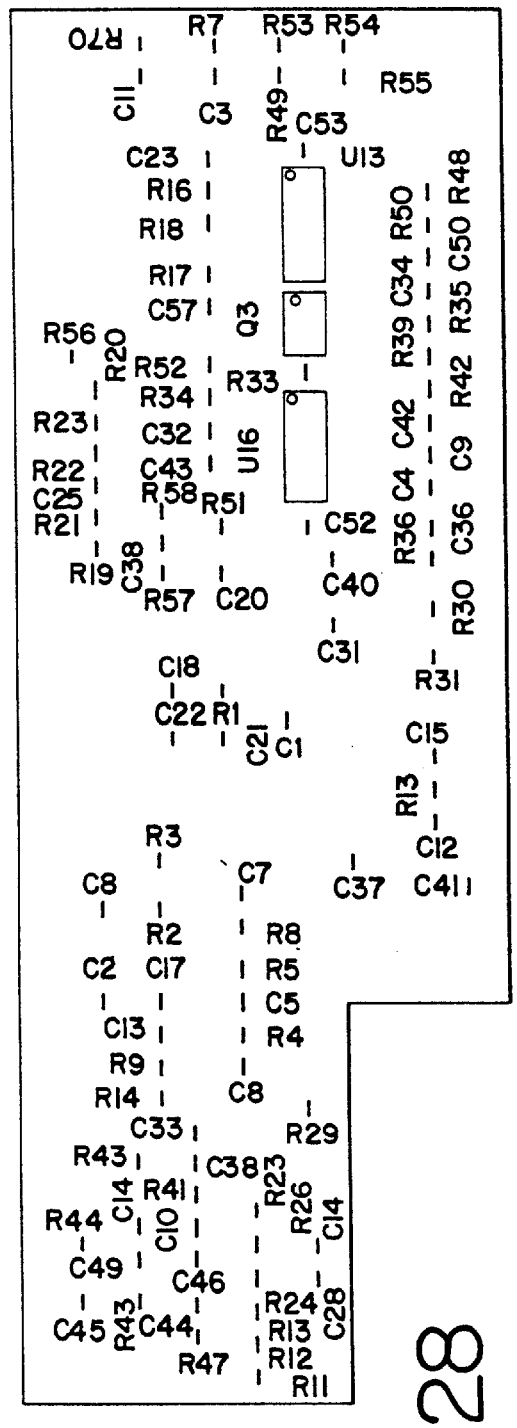
Figure 29A:
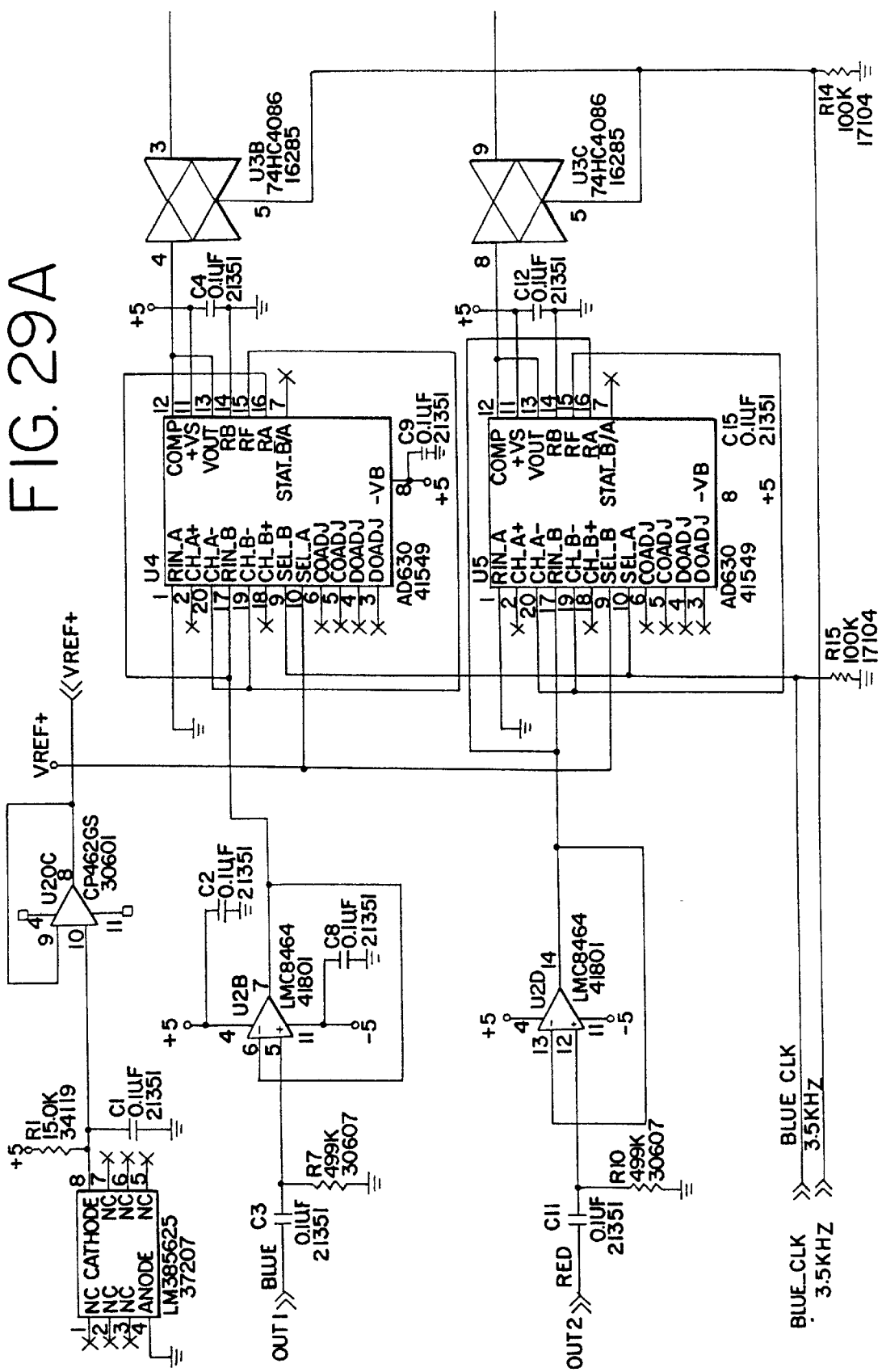
FIGS. 29A–D and 30A–C are circuit diagrams for the main pc board for the transfer device of FIG. 1.
Figure 29B:
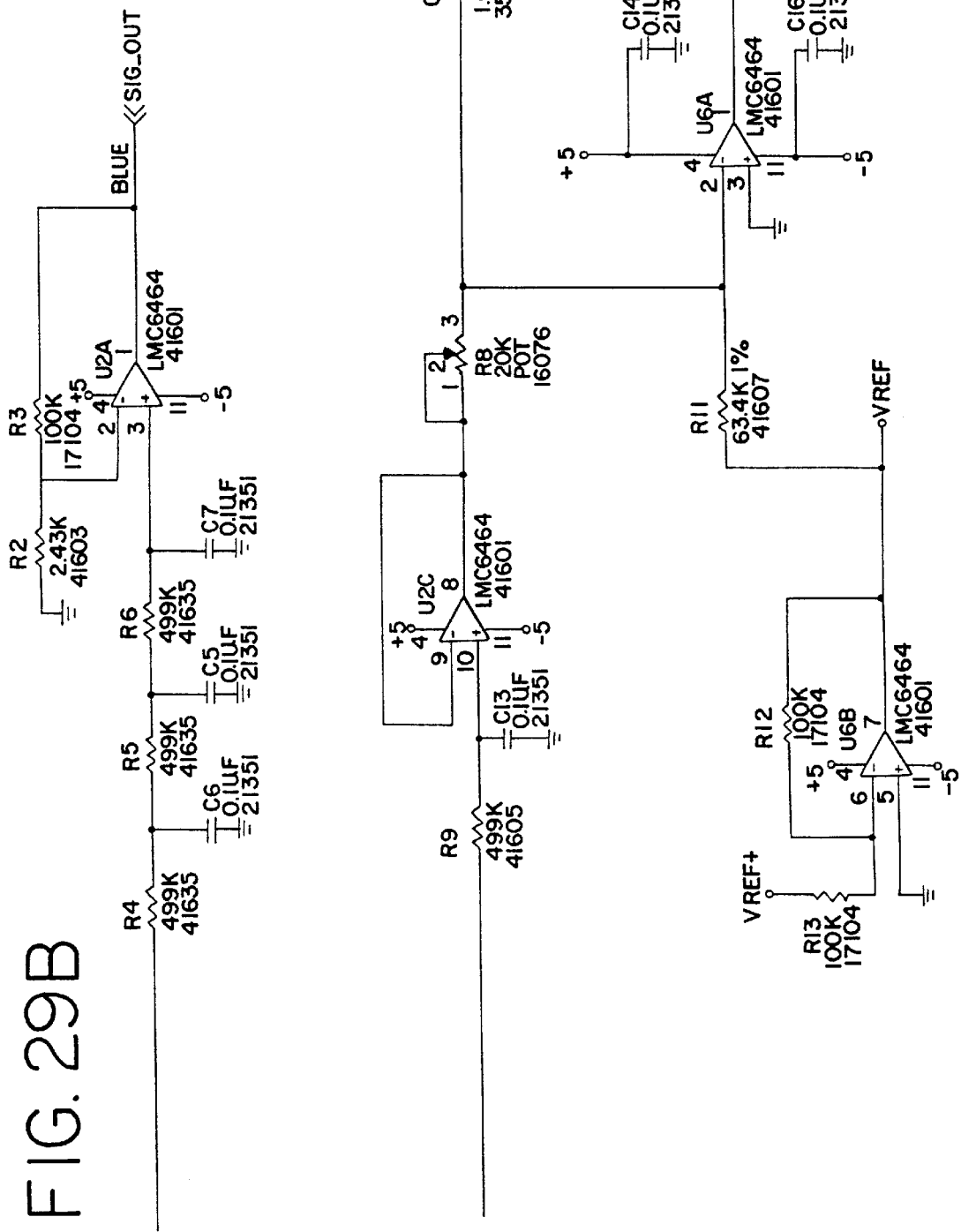
Figure 29C:
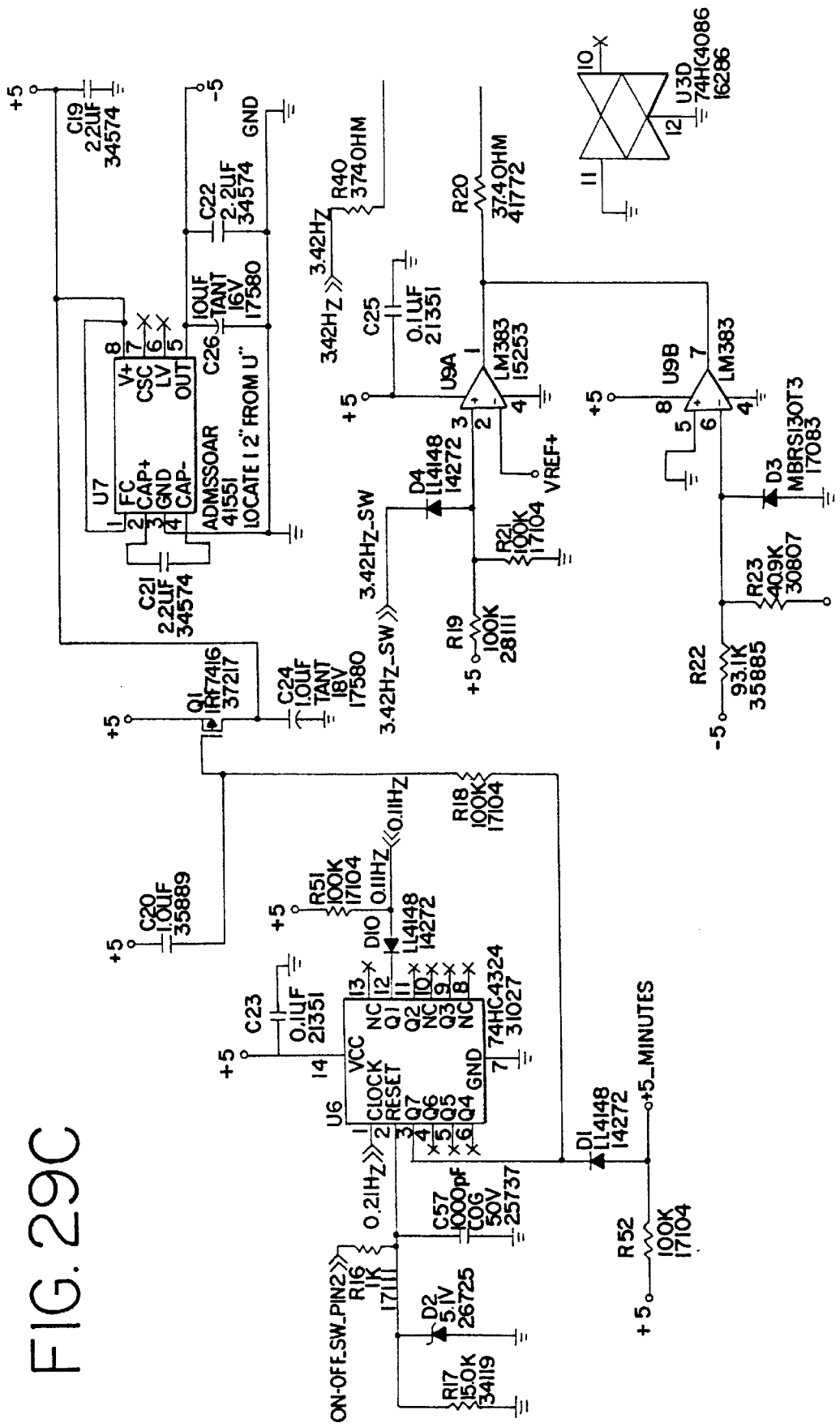
Figure 29D:
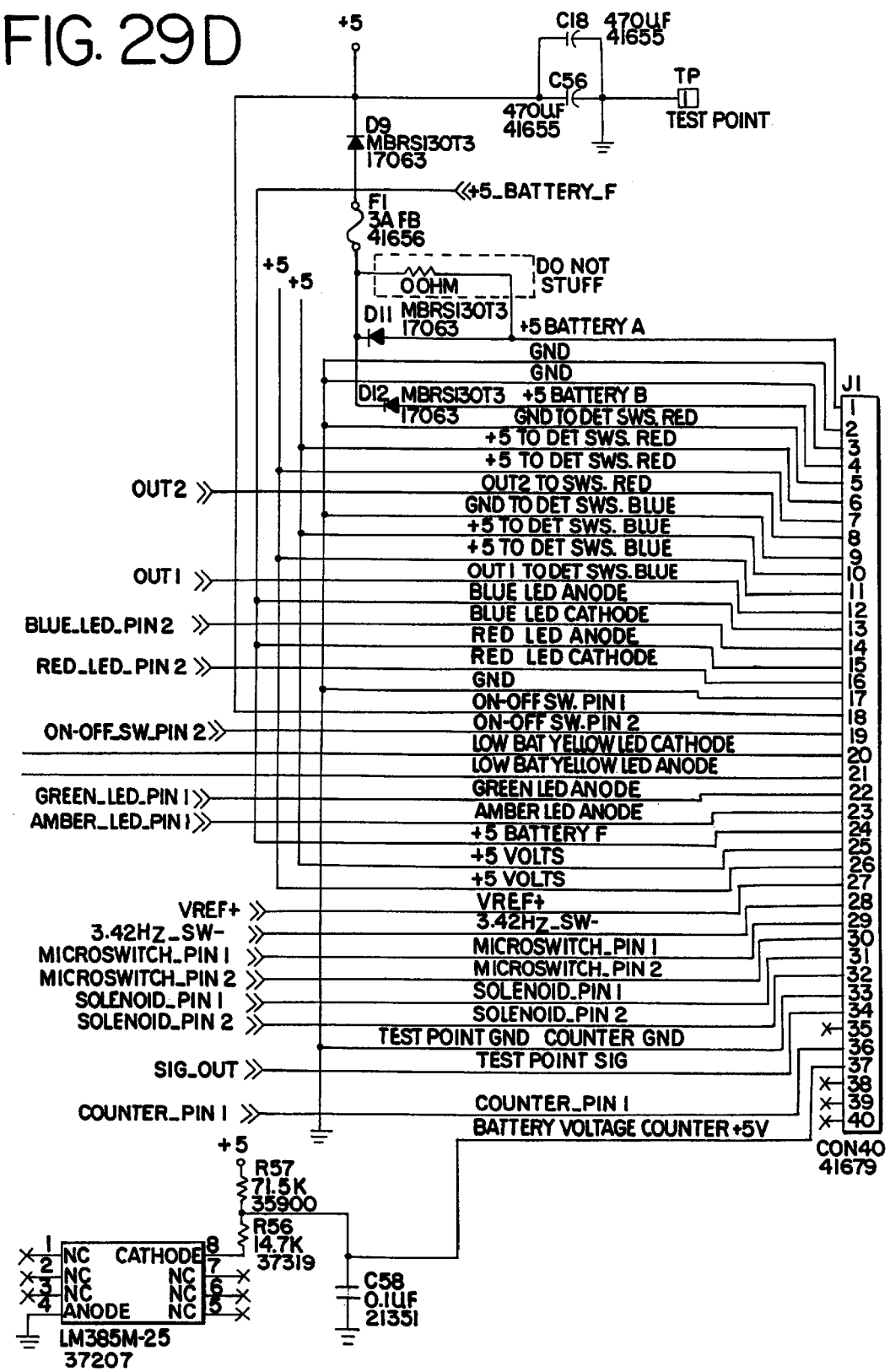
Figure 30A:
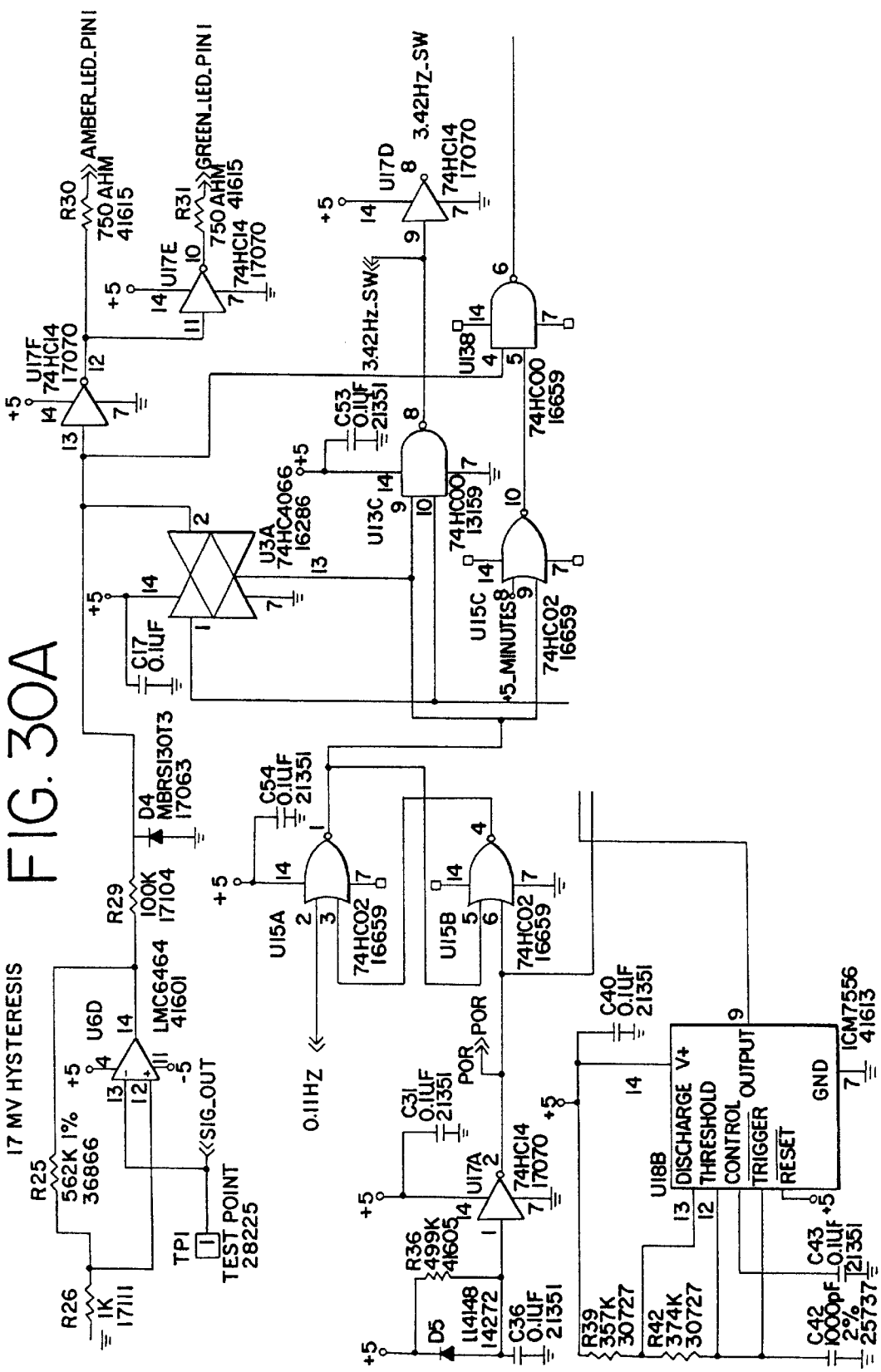
Figure 30B:
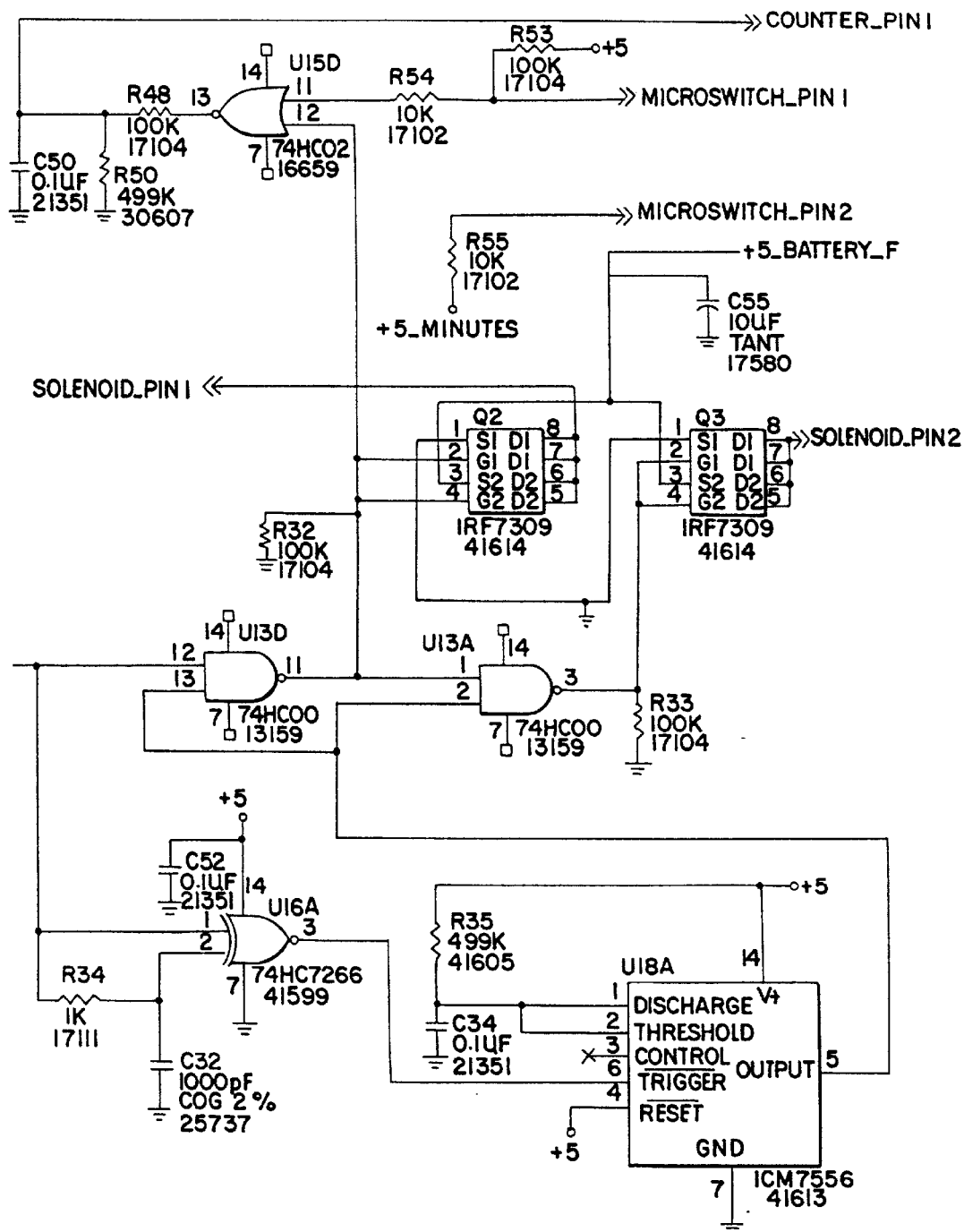
Figure 30C:
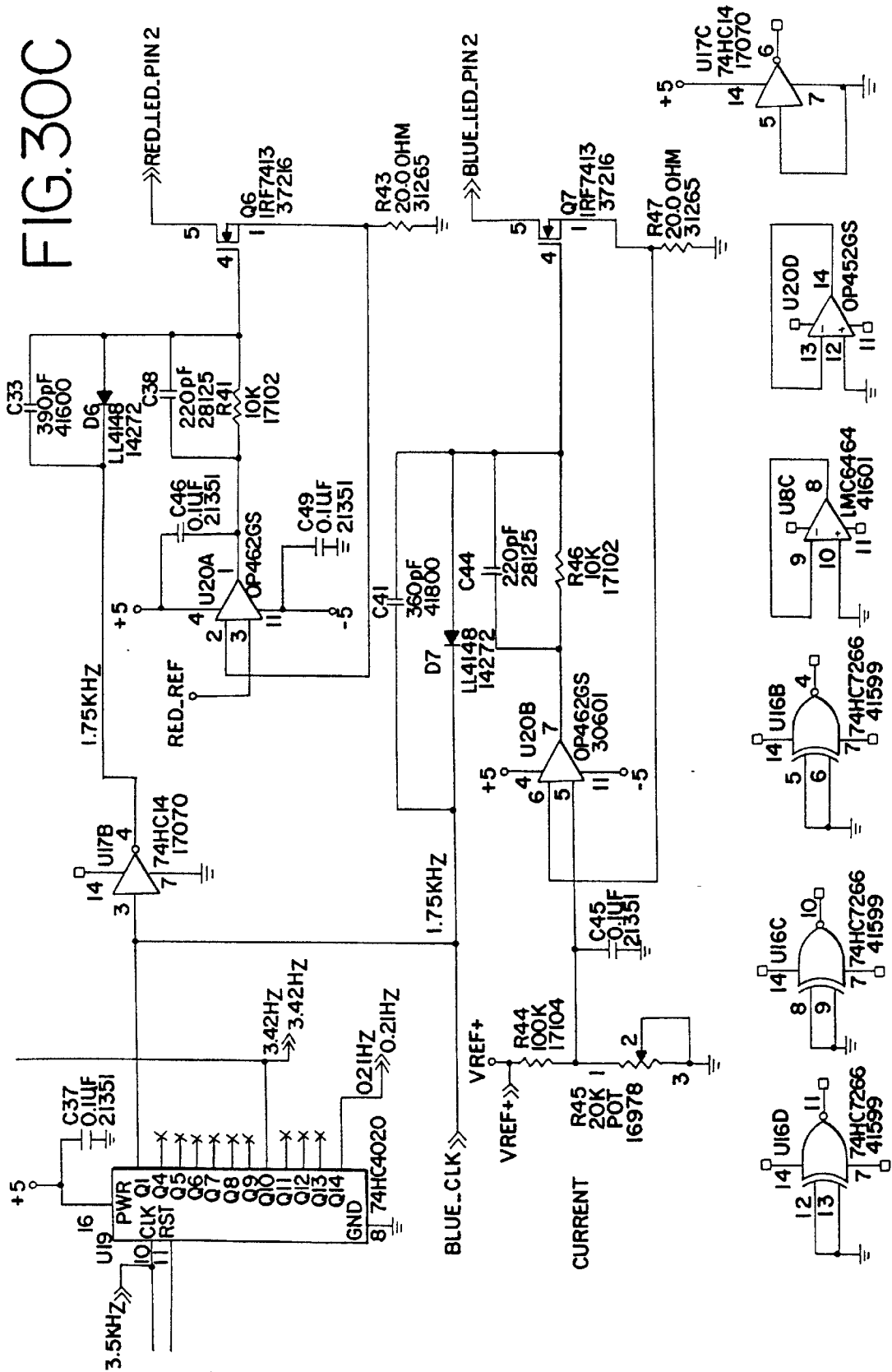

The pressure indicator of the present invention consists of an electronic pressure sensing and display circuit that is mounted on the pressure indicator circuit board 58. The primary and secondary sides of the pressure indicator circuit board, which can be seen in FIGS. 24 and 25 respectively. The schematic diagrams of the electronics on the pressure indicator circuit board 58 are shown in FIGS. 26A–B. A pressure transducer 60 mounted on the pressure indicator circuit board 58 is connected to the fluid entry port 46. When the pressure sensing circuit is on, the pressure transducer 60 measures the pressure of the fluid as it flows into the transfer device 12. The pressure sensing circuit converts the pressure measurement to a voltage reading and determines which of the pressure indicator LEDs 28a–d located on the top portion of the pressure indicator circuit board 58 to illuminate to indicate the pressure range of the applied fluid force. For safe operation of the intraluminal radiation treatment system, it is preferred that the first yellow LED 28a is illuminated when the pressure exceeds 6 psi; the second yellow LED 28b is illuminated when the pressure exceeds 10 psi; the third yellow LED 28c is illuminated when the pressure exceeds 60 psi; and the red LED 28d is illuminated when the pressure exceeds 80 psi. Therefore, the first and second yellow LEDs 28a,b are illuminated when the pressure is above 10 psi, all three yellow LEDs 28a–c are illuminated when the pressure is above 60 psi, and the red LED 28d and all three yellow LEDs 28a–c are illuminated when the pressure is above 80 psi.

As seen in FIG. 3, lettering, markings, and/or international symbols are placed on the exterior of the transfer device 12 next to the LED windows to indicate to the user which LEDs should be illuminated to provide the appropriate pressures for transferring the treatment elements to and from the catheter and the appropriate pressures for maintaining the treatment elements at the distal end of the catheter for the duration of the treatment. The pressure for maintaining the treatment elements at the distal end of the catheter is much less than the pressure required to quickly send and retrieve the treatment elements. The treatment elements can be maintained at the distal end of the catheter with a force between 6 and 10 psi. The illumination of only the first yellow LED 28a indicates that an appropriate pressure for maintaining the treatment elements at the distal end of the catheter is being applied. The optimum pressure range for the transference of treatment elements to and from the catheter is between 60 and 80 psi. The illumination of the first and second yellow LEDs 28a,b indicates that the treatment elements are being transferred with a force somewhere between 10 and 60 psi, and the illumination of all three yellow LEDs 28a–c indicates that the treatment elements are being transferred in less time with a force between 60 and 80 psi. Either of these pressure ranges can be used as a guideline to safely transfer the treatment elements. However, the illumination of the red LED 28d and the three yellow LEDs 28a–c indicates to the user that the fluid pressure is at an unsafe level (greater than 80 psi) and that there is an immediate need to reduce the applied force to a safe level as indicated by the pressure indicator LEDs 28a–d.

In addition to the pressure sensing circuitry and the pressure indicator LEDs 28a–d, the power button 22, the low battery indicator LED 30 and the treatment element indicator LEDs 32a,b are mounted to the pressure indicator circuit board 58. All of the LEDs and the power button 22 are electronically coupled to a main printed circuit board 62 mounted to the underside of the chassis 20. When the electronics are powered up, a timer 846 located on the main circuit board 62 flashes all the LEDs for a very short duration of time to indicate that the LEDs are functional. A transparent silicone member or light pipe 66, is placed over the top of the pressure indicator circuit board 58. The light pipe 66 has raised areas shaped to fit over the LEDs and thus fit within the respective openings of the upper shell. The light pipe 66 protects the components while allowing the light of the LEDs to pass so as to be visible to the user. The power button 22 fits through an opening in the light pipe 66 to mate with the appropriate opening in the upper portion of the transfer device exterior.

As discussed previously, the low battery indicator 30 located on the pressure indicator circuit board 58 is connected to the low battery indicator circuitry on the main circuit board 62. Two comparators monitor the +5 and −5 volt power supply voltages. Low battery conditions are set at below +5.1 volts and/or below −5.0 volts. During low battery conditions the low battery indicator 30 flashes continuously at a set frequency when the transfer device 12 is powered. The low battery indicator light 30 is identified by a low battery icon or international symbol located adjacent to it on the surface of the upper shell (FIG. 3).

The pressure relief valve 56 is specially designed for use with the transfer device 12 and has an activation pressure of 100±15 psi. The pressure relief valve 56 comprises a housing 68, a piston or other valve element 70, an o-ring 72, a spring 74, and a spring retainer 76. The housing 68, as seen in FIG. 10, has an interior fluid passageway 78 along its entire length. Each end of the pressure relief housing 68 mates with a fluid connector 80 (FIG. 12). Distal to the fluid inlet of the housing, the housing has an interior surface that tapers outwardly to create a valve seat 82. The interior surface then steps up to a slightly larger diameter, creating a shoulder 84, and continues in a straight path to the fluid outlet of the pressure relief housing 68. A proximal portion of the piston or valve element 70 is tapered to mate with the valve seat 82 to provide a fluid tight seal. The tapered portion 86 of the piston or valve element 70 preferably has an annular groove 88 for placement of the seal or o-ring 72 to assist in providing a fluid tight seal. As seen in FIG. 11, the groove 88 may be created such that its top and bottom surfaces angle downward from the central axis of the valve element 70 to a position perpendicular to the piston's or valve element's tapered exterior surface 86. Such a groove 88 may help to maintain proper o-ring placement and create a firmer seal as the piston 70 is forced to and from its seated position. The exterior surface of the piston or valve element 70 then steps up to a slightly larger diameter creating an annular flange 92. When the valve element 70 is in a closed valve position, the annular flange 92 rests on the annular shoulder 84 of the housing 68. This interaction between the flange 92 and shoulder 84 prevents over compression of the valve element 70 along the tapered valve seat 82. The slightly larger diameter portion 94 of the valve element 70 loosely fits the stepped diameter portion 96 in the housing 68 so as to allow fluid flow to pass around it. If necessary, portions of the larger diameter exterior surface of the piston may be shaped or removed to provide a larger passageway for fluid flow. One example could be to create flat sides 98 around the periphery of the larger diameter portion 94 of the piston 70. The distal portion 100 of the piston or valve element 70 then steps down to a smaller diameter. The proximal portion of the spring 74 is positioned over the distal portion 100 of the piston or valve element 70 and is held in the appropriate compressed state (pre-calibrated to provide a seal strength of 100±15 psi) by the spring retainer 76, which is preferably a retention or set screw having a through hole for fluid passage. The retention screw has external threads and is screwed into the distal portion of a housing 68. System pressure above 100±15 psi is sufficient to unseat the piston 70/o-ring 72 combination and allow the fluid to flow through the valve 56 and exit the transfer device 12 through the fluid exit port 52 into an external fluid reservoir (not shown). Otherwise, the spring 74 biases the piston 70/o-ring 72 combination into a seated position, thereby blocking flow through the valve 56 and allowing flow to continue to be safely directed through the system.

Figure 14:
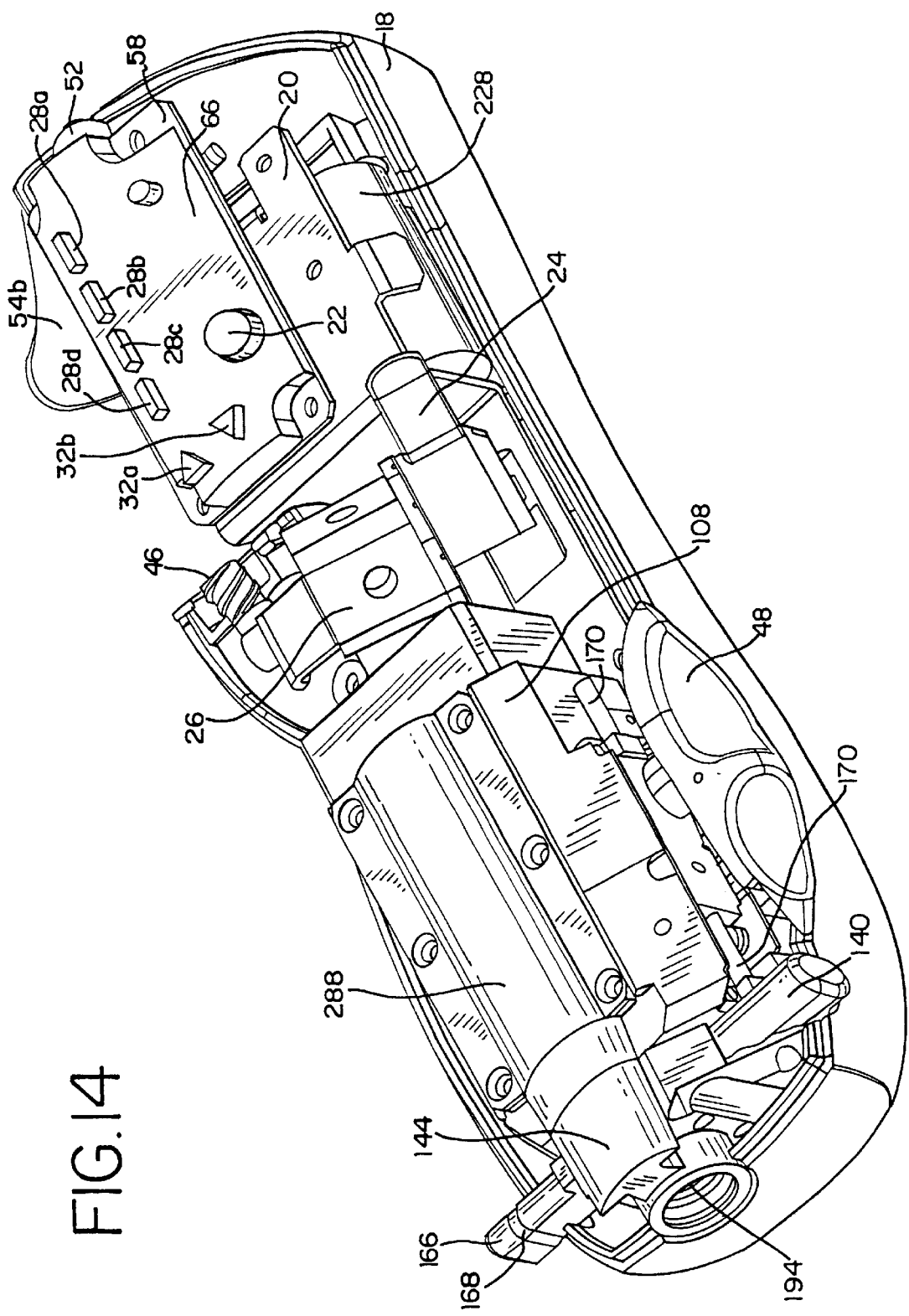
FIG. 14. is a perspective view of the transfer device of FIG. 1 with the top half of the housing removed to show detail.

The appearance and functionality of fluid control valve 26 in FIGS. 8 and 14 are identical to that of the fluid control valve disclosed in Ser. No. 08/936,058, filed Sep. 23, 1997 and identified therein as fluid control valve 512 in FIG. 48. The fluid control valve 26 of the present transfer device 12 directs the fluid flow of the system which can be manipulated by moving the flow control switch 24 between detented send, return, and neutral positions. The valve 26 may comprise four ports 102 and should be capable of withstanding the system's highest operating pressure (i.e. at least 100 to 115 psi), such as valve part no. 0162336 (HV4-4, w/.040 ports), manufactured by the Hamilton Company of Reno, Nev.

Figure 9:
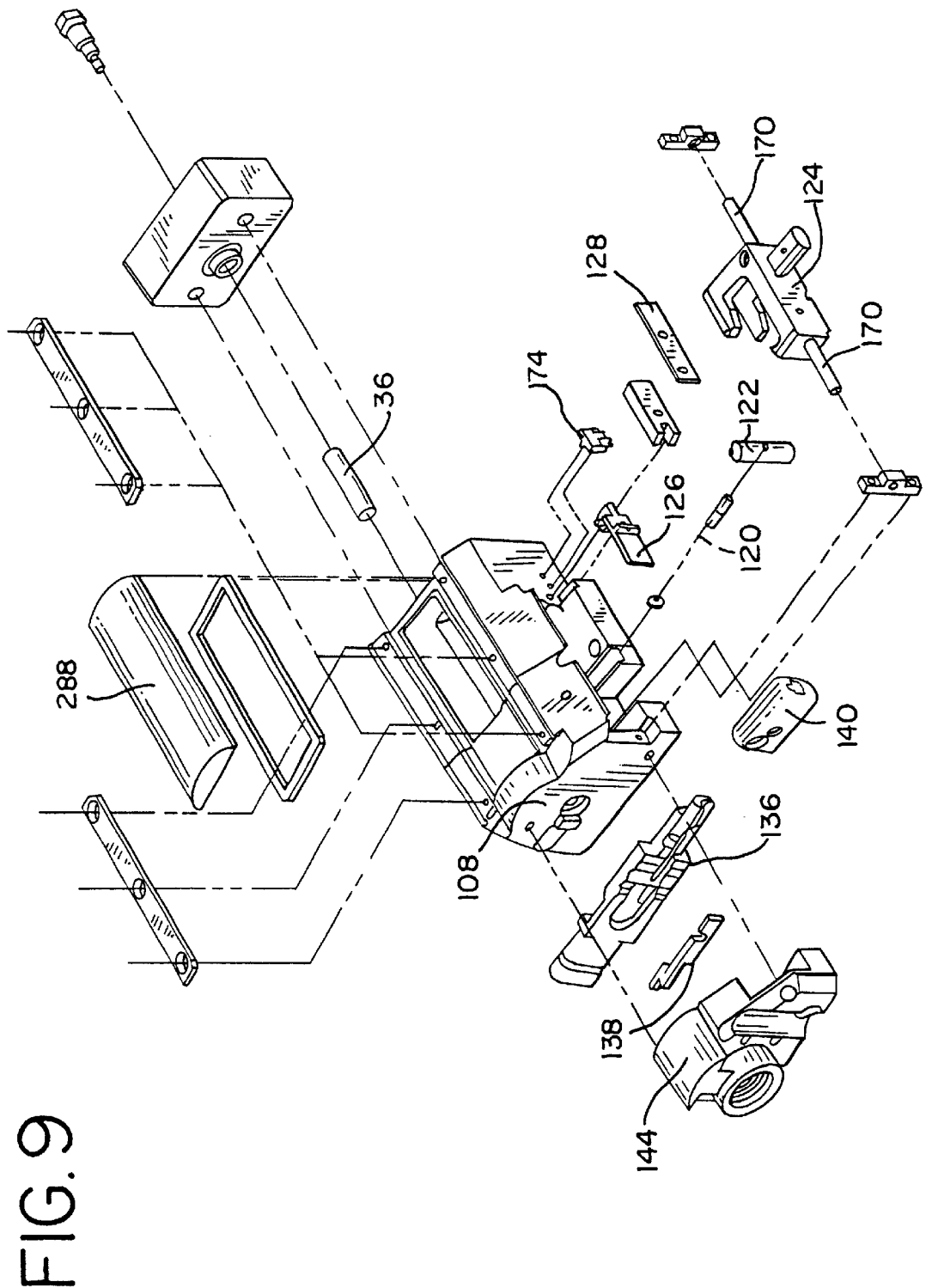
FIG. 9 is a further exploded perspective view of selected internal components of the transfer device of FIG. 1.

As indicated above, the interior components of the transfer device 12 are constructed separately and mounted to the chassis 20, where they are joined together for fluid communication by means of tubing 104 and barbed connectors 106 as shown in FIG. 8. The fluid tubing 104 should be kink resistant and capable of withstanding the system operating pressures without significant fluid leakage. Examples of such tubing include annealed polyurethane tubing and annealed PVC tubing. FIG. 12 is a flow control diagram that visually explains fluid flow of the system. Turning to FIG. 9, the transfer device 12 further includes a separate block member 108 which is mounted to the chassis 20 and houses the quartz sleeve 36, a pin gate mechanism 110, and the optics portion of a seed verification system. The block member 108 has a mated projection 112 that is machined below the surface of the block member 108 such that it is recessed within a cavity (not shown). This simplified design reduces the number of components by allowing an o-ring groove 116 to be cut directly into the wall of the cavity that surrounds the mated projection 112. Preferably, all or a portion of the block member 108 is painted black (dark color) or is made of a black (dark) material, such as black acrylic. This will lessen unwanted reflectivity of light and thus, will increase the accuracy of the electronic source sensing system, as discussed in detail below, and will increase the visibility of the treatment elements to the user.

The block member 108 may contain a spring loaded assembly (not shown) to hold the quartz sleeve 36 in its proper position (in alignment with the optics for proper seed detection) even when the transfer device 12 is dropped. A lumen 118 extends along the length of the quartz sleeve 36 for storage of the treatment elements and marker seeds when they are not being used to deliver radiation therapy. The quartz sleeve 36 shields the user from beta particles emitted by the treatment elements when stored therein, thus enabling a user to safely handle the transfer device 12. The distal end of the quartz lumen 118 preferably has a chamfer to prevent seed hang-ups when they are being transferred. The entire length of the quartz sleeve 36 can be seen through an opening in the block member 108 which is aligned with the viewing window 34. To provide even better visibility of the treatment elements and marker seeds within the quartz sleeve 36, a colored material may be adhered to or placed under the bottom of the quartz sleeve 36. Alternatively or additionally, the bottom of the quartz sleeve 36 may be textured (for example, by bead blasting) to create a background for enhanced viewing of the treatment elements.

The pin gate mechanism 110 consists of a pin gate 120, cylindrical pin head 122, slider block 124, pivoting lock 126, leaf spring 128, and leaf spring block 130 all working together to position the pin gate 120 in an extended (closed) or retracted (open) position relative to the lumen 118 just distal of the quartz sleeve 36 for respectively blocking or permitting passage of treatment elements. The components and functions of the pin gate mechanism 110 are identical to that of the pin gate mechanism disclosed in Ser. No. 08/936,058, filed Sep. 23, 1997, now U.S. Pat. No. 6,013,020, and identified therein by reference numeral 352. However, the pin gate mechanism 110 of the present invention provides an additional safety feature for preventing the pin gate 120 from closing onto and damaging a treatment element. If an attempt to close the pin gate 120 is made while a treatment element is in the pathway of the pin gate 120, the pivoting lock 126 is oriented in such a way that it does not clear the pathway of the moving slider 124 and prevents any further advancement of the slider 124, which in turn halts the downward motion of the pin 120 onto the treatment element. Alternatively, the pin gate mechanism 110 may be positioned such that the pin gate 120 is extended and retracted into the distal end of the quartz lumen 118 through a radial channel extending from the top of the quartz sleeve 36 and intersecting with the quartz lumen 118.

The present transfer device 12 includes a latch mechanism (shown in FIGS. 9 and 14) for receiving, locking, and properly seating the catheter connector in the transfer device. The components of the latch mechanism include a latch body 136, a latch sear 138, a latch button 140, and two ball and spring plungers (not shown), all of which reside in between the block member 108 and end body 144 of the transfer device 12. As illustrated in FIGS. 9, the latch body 136 is generally rectangular with an elongated opening as seen from its distal face and a raised portion with a U-shaped recess as seen on its proximal face. The U-shaped recess is adjacent to the elongated opening, extends partially along the opening's length, and is accessible therethrough. Because the U-shaped recess is smaller than the elongated opening, some of the raised U-shaped portion surrounding the recess overlaps a portion of the elongated opening. The latch body 136 is preferably made from an opaque material (such as Delrin) to provide lubricity between it and the polycarbonate or acrylic pieces (i.e. block portion 108 and end body 144) with which it will be in sliding contact. The latch sear 138 fits within a similarly shaped recessed portion along the proximal face of the latch body 136 such that the small end 148 of the latch sear 138 extends within the elongated opening. The latch button 140 houses a compression spring 150 and slides over the upper ends 152 and 154 of the latch sear 138 and latch body 136 such that the latch sear 138 and compression spring (not shown) is in contact with one another and the latch button 140 is secured to the latch body 136. The ball and spring plungers 142 extend from shallow bores within the end body 144 such that each of the two balls rests within one of the valleys along the proximal face of the latch body 136 in between the elongated opening and the extended portion with the through hole. connector 158 with the U-shaped portion 146 that overlaps the elongated opening in the latch body 136. As the latch body 136 is moved from the unlatched position to the latched position, the ball of each of the two ball and spring plungers 142 is ramped onto one of the peaks adjacent the valleys on the proximal face of the latch body 136. This ramping causes the spring biased plungers 142 to compress and force the latch body 136 and engaged connector 158 toward the mated projection 112 at the distal end of the block member 108; thus, ensuring that a chamfer 162 on a connector insert 164 is completely seated against the projection 112 and in complete alignment with its opening. As an indication that the connector 158 has been fully engaged, the free end 166 of the latch body 136 (opposite that end connected to the latch button 140) pops out from the side of the transfer device 12. If a band 168 or other marking on the free end 166 is fully visible, then the user can be sure that the connector 158 is now locked into the transfer device 12. To disengage the connector 158 from the transfer device 12, the free end 166 of the latch body 136 is pushed inward to remove the U-shaped portion from the relieved area of the connector 158.

To provide a safer transfer device, an interlock mechanism exists between the latch body 136 and the slider block 124. The slider block 124 slides toward the distal end of the transfer device 12 to retract the pin gate 120 and, thus, allows the treatment elements to be delivered out of the transfer device 12. To enable this movement, the shaft 170 extending from the distal end of the slider block 124 and the through holes of the latch button 140, latch sear 138, and latch body 136 must all be in alignment. When the latching mechanism 134 is in the unlatched position, regardless of whether or not a connector 158 is inserted into the transfer device 12, the extending shaft 170 does not align with the through holes and additionally, the actuator switch 48 is impeded by the popped up latch button 140. When the latching mechanism 134 is in the latched position and no connector 158 is locked into the transfer device 12, the through hole in the latch sear 138 does not completely align with the through hole in the latch button 140 and movement of the slider block 124 is impeded by the latch sear 138. However, when the connector 158 is inserted into the transfer device 12 and the latch body 136 is slid toward the connector 158 for engagement purposes, the small end 148 of latch sear 138 collides with the connector 158 just above the connector's relieved portion 172 and is forced toward the latch button 140 and against the spring 150 such that the through hole of the latch sear now aligns with both the latch body through hole and the latch button through hole. Thus, the pin gate 120 can only be retracted to an open gate position when the connector 158 is inserted into the transfer device 12 and fully engaged by the latching mechanism 134.

Furthermore, when the necessary conditions are met and the shaft 170 extends through all three holes, the latch body 136 cannot be slid back to the unlatched position, thus preventing the latch body 136 from disengaging the relieved portion 172 on the connector 158. As an extra safety caution and a visual reminder to the user that the connector 158 is not to be disengaged from the transfer device 12 while the pin gate 120 is in a retracted position, the actuator switch 48 is configured to at least partially cover the latch button 140, thus preventing the latch body 136 from being moved into the unlatched position.

A counter has been added to the transfer device 12 to keep a running total of the number of uses of the intracoronary radiation treatment system. The counter comprises a microswitch 174 that is mounted on or adjacent to the block member 108 to interact with either the proximal or distal end of shaft 170 of the slider 124. In either location, the microswitch 174 is electronically coupled to a counter circuit on the main circuit board 62. If the microswitch 174 is positioned near the proximal end of shaft 170, the shaft 170 trips the microswitch 174 as the slider 124 and pin gate mechanism 110 lock into the closed position. In addition to the microswitch 174 being tripped, two other conditions must be satisfied. First, the electronics must be on, and second, the green seed sensing LED 32a must be illuminated as the amber seed sensing LED 32b is extinguished (an indication that the treatment elements have been returned to the quartz housing). If the microswitch 174 is positioned near the distal end of shaft 170, the shaft 170 trips the microswitch 174 as the slider 124 and pin gate mechanism 110 lock into the open position. In addition to the distally placed microswitch being tripped, two other conditions must be satisfied. First, the electronics must be on, and second, the amber seed sensing LED 32b must be illuminated as the green seed sensing LED 32a is extinguished (an indication that the treatment elements have left the quartz housing). Each time all three conditions are met, the number on a miniature electronic counter display 44 (see FIG. 4 of bottom housing) will increase by one.

As an added safety feature, an electromagnetic locking mechanism interacts with the slider block 124 to prevent the opening or closing of the gate 120 when the seed sensing indicator LEDS 32a, 32b indicate that not all of the treatment elements and marker seeds are within the quartz housing 36 (amber LED 32b is illuminated and green LED 32a is not). The electromagnetic locking mechanism may be a solenoid 176 that is battery operated and has minimal current draw such as magnetic latching solenoid type SCL1330-001 manufactured by Bicron Electronics Company. Such a solenoid comprises a coil, a magnet and a plunger 178 residing in a frame. The solenoid may also include a spring to assist in forcing the solenoid plunger 178 in either an extended or retracted position. The plunger 178 extends or retracts based on the direction of electricity through the coil. The current flow in one direction creates a negative polarity in which the plunger 178 and magnet repel one another. The current flow in the opposite direction creates a positive polarity in which the plunger 178 and magnet attract one another.

Figure 15:
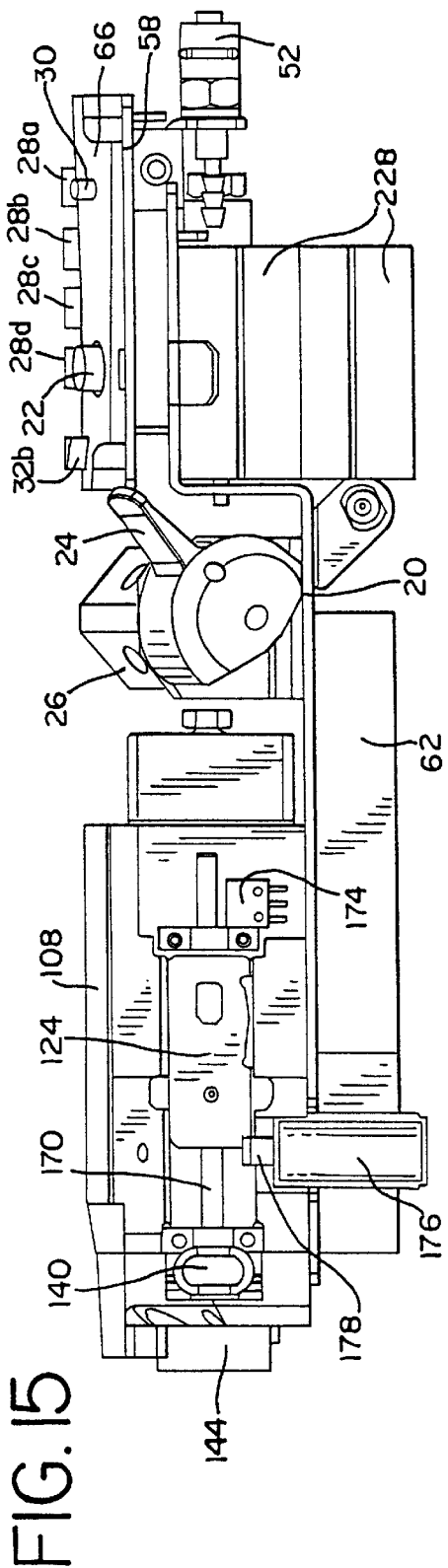
FIGS. 15 and 16 are plan views of selected interior components of the transfer device of FIG. 1.
Figure 16:
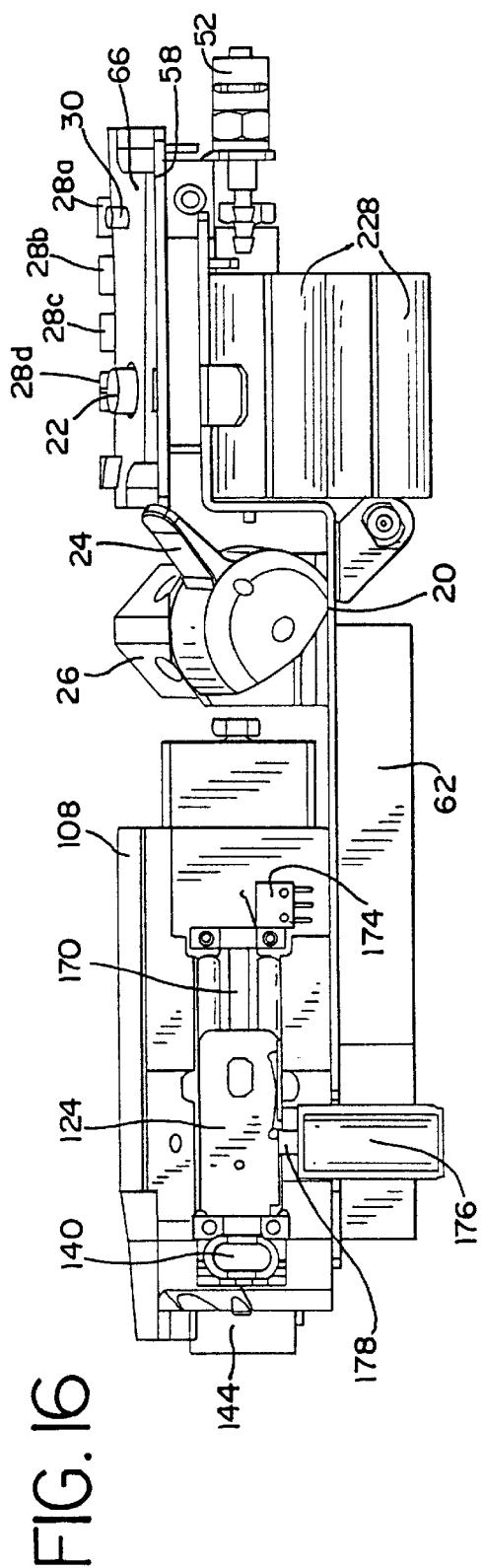

The solenoid 176 is mounted on the chassis 20 perpendicular to and below the slider 124. The solenoid 176 is connected to a solenoid driver which in turn is connected to the seed sensing indicator LED drivers 32a, 32b and the five minute timer 180, all of which are located on the main circuit board 62. When the amber seed sensing LED 32b is lit, indicating that fewer than all the treatment elements and marker seeds are within the quartz housing 36, the solenoid plunger 178 extends into a recess or hole in the slider 124 and impedes movement of the slider 124. As seen in FIG. 15, the plunger 178 is extended and prevents the slider 124 from being shifted to an open gate position when the amber LED 32b is lit. As soon as the amber LED 32b is extinguished and the green LED 32a is illuminated, the plunger 178 retracts and allows the slider 124 to move into the open gate position. As seen in FIG. 16, the slider 124 is in the open gate position and the solenoid plunger 178 is extended and is preventing the slider 124 from moving into a closed gate positioned when the amber LED 32b is lit. As soon as the amber LED 32b is extinguished and the green LED 32a is illuminated, the plunger 178 is retracted to allow movement of the slider 124 into the closed gate position. When the five minute timer 180 turns off the electronics, the plunger 178 is extended, locking the slider 124 into its present position.

Turning to FIGS. 17, 21 and 22, the catheter connector 158, which comprises a further aspect of the present invention, is provided with detents 182 that interlock with an annular shoulder in the end body 144 of the transfer device 12, and must be manually actuated to withdraw the catheter connector 158 from the transfer device 12 after it has been unlatched by the latching mechanism. The catheter connector 158 includes a central plug portion 184 having a through lumen 186 and cantilever arms 188, a connector insert 164 which is received by central plug through lumen 186, and a skirt 190 that fits over the distal portion of the connector 158, but which remains outside of the transfer device 12 when the connector 158 is fully connected thereto. The connector insert 164 and central plug portion 184 may be identical to the one described in Ser. No. 08/936,058, filed Sep. 23, 1997, now U.S. Pat. No. 6,013,020. Alternatively, the central plug portion 184 may have the wall between the two-o-rings taper inward from both ends to enhance the sealing effects of the o-rings. The skirt 190 is threaded over the catheter tubing and then, after the connector 158 is bonded to the catheter tubing, it is fitted over a distal portion of the connector 158 which includes the cantilever arms 188. When the connector 158 is fully inserted into the transfer device 12, the skirt 190 covers the slotted portions 192 that remain external to the transfer device 12, abuts the distal tip of the transfer device 12, and surrounds the connector entrance 194 to the transfer device 12. These characteristics of the skirt 190 serve to maintain sterility of the distal portion of the connector 158 as well as prevent foreign matter from contacting the connector entrance 194 to the transfer device 12 through the slotted portions 192 of the central plug 184. The skirt 190 preferably has two opposing rectangular sides 196 for mating with the depressible sides of the cantilever arms 188 and for indicating to the user where to manipulate the cantilever arms 188. The skirt 190 is preferably made of silicone or other material that is flexible enough to permit manipulation of the cantilever arms 188 as the connector 158 is pulled out of the transfer device 12. In addition, the rectangular sides 196 may be thinner than the rest of skirt 190 so as to provide for easier manipulation of the cantilever arms 188. Having to depress the arms 188 while simultaneously pulling on the connector 158 provides a further safety feature for preventing inadvertent withdrawal of the connector 158 from the transfer device 12.

As seen in FIG. 1, catheter 14 of the present invention connects to the transfer device 12 by catheter connector 158, best seen in FIG. 21, to permit delivery of the treatment elements to a selected site within a patient. The catheter has a proximal end, a distal end, and an elongated portion therebetween. Referring to FIGS. 18–20, the distal portion of the catheter consists of three lumens: a seed lumen 198, a fluid return lumen (not shown), and a guidewire lumen 200. The proximal portion of the catheter 14 consists of three lumens: the seed lumen 198, the fluid return lumen (not shown), and a stiffening lumen 202. The seed lumen 198 and the fluid return lumen are contiguous from the proximal end of the catheter 14 to the distal end of the catheter 14 and communicate with one another at the distal end of the catheter 14 through an intraluminal connector 204 which is located in the seed lumen 198 (FIG. 20). The intraluminal connector 204 is preferably made of stainless steel and also reinforces the distal end of the catheter 14 to prevent the treating elements from exiting the distal end of the catheter 14. The guidewire lumen 200 at the distal portion of the catheter 14 has an opening 206 at its distal tip 208 and extends between the opening and a guidewire exit port 210 along the sidewall of the catheter 14. The guidewire exit port 210 may be located at any point along the catheter 14, but is preferably located 30 to 40 cm proximal to the distal most portion of distal tip and significantly distal to the proximal end of the catheter 14. The distal guidewire exit port 210 provides for rapid exchange delivery of the catheter as it is being guided over a guidewire to a selected site. The stiffening lumen 202 of the proximal portion of the catheter 14 extends from the proximal end of the catheter 14 to just proximal of the guidewire exit port 210 and contains a stiffening wire or mandrel 212 that provides support for the proximal portion of the catheter 14 during insertion, manipulation, and withdrawal of the catheter 14. As seen in FIGS. 21 and 22, the proximal end of the stiffening wire 212 is securely embedded in the catheter connector 158. The stiffening wire 212 extends from the connector 158 to the near vicinity of the guidewire exit port 210, or may extend to a point slightly distal of the guidewire exit port 210 to provide additional support during catheter manipulation. For optimum support, the stiffening wire 212 is preferably made of stainless steel round wire. To provide for greater flexibility near the guidewire exit port 210, the stiffening wire 212 may have a gradual taper or flattened configuration at its distal end.

During the manufacture of the rapid exchange catheter 14, polyethylene beading 214 is placed within the stiffening lumen 202 just proximal to the guidewire exit port 210 and is fused to the luminal walls so as to provide a barrier between the stiffening wire 212 and the guidewire exit port 210. Prior to the fusing process, a small piece of tubing 216 (preferably low density polyethylene) may be inserted into the guidewire lumen 200 and positioned adjacent the guidewire exit port 210. A mandrel 218 may then be inserted into the distal end of the guidewire lumen 200, through the piece of tubing 216, and through the guidewire exit port 210 to the exterior of the catheter 14 (FIG. 19). As a result of the fusing process, the tubing 216 collapses around the mandrel 218 and fills in and around the guidewire exit port 210 to become an integral part of the guidewire lumen 200 (FIG. 18). The channel created by the mandrel gradually inclines toward the exterior of the catheter 14 to provide a ramp for directing the guidewire out of the guidewire exit port 210 as it is being inserted through the distal end of the guidewire lumen 200. The top of the fused tubing 216 may need to be skived off to expose at least a portion of the channel to the exterior of the catheter 14 to recreate the exit port. Also, the tubing 216 may be of a color readily distinguishable from the rest of the catheter 14 so that the location of the guidewire exit port 210 is easily identifiable to the user.

The catheter 14, its seed lumen 198, and its guidewire lumen 200 are all of a generally round cross-section. The fluid return lumen, however, has an elliptical cross-section to increase the area for fluid flow without compromising the outer diameter of the catheter 14. The greater area lowers the pressure required to send maintain, and return the treating elements. It also decreases the time it takes to transfer the treating elements from the transfer device 12 to the distal end of the catheter 14 and vice versa. However, the fluid return lumen may be of any size or shape to provide for optimal transfer of the treating elements using a limited volume of fluid. Preferably, the catheter fluid lumens (especially the fluid return lumen) are dimensioned to provide treatment element send and return times each in the range of three to ten seconds and more preferably within one to six seconds, while not exceeding a 5 French outer catheter diameter, not exceeding a pressure of 100 psi, and using not more than 20 cc fluid to send, maintain, and return the treatment elements.

For uniform dosing, it maybe determined that the treating elements need to be positioned at or near the center of the luminal wall. In this case, the seed lumen 198 may need to be positioned as close as possible to the center of the catheter 14 to prevent the seed lumen 198 and radioactive elements from lying too close to one side of the luminal wall.

The catheter 14 is preferably made in a single extrusion of 100% low-density polyethylene, which is very flexible, soft and lubricous. These characteristics allow the catheter 14 to be inserted over a guide wire and into an endoluminal area within the human body without damaging the luminal walls. If a catheter 14 made of 100% low density polyethylene is too soft or pliable, then a polyethylene blend which consists of a certain percentage of both high and low density polyethylene may be used. To maintain flexibility of the catheter 14, the polyethylene blend must have a higher percentage of low-density polyethylene.

Turning to FIG. 20, an atraumatic tip 208 having a small taper (preferably 11 degrees or less and most preferably 5 degrees) and a small distal tip radius is fused (possibly with radiofrequency energy) to the distal end of the catheter 14. The fusing process closes the distal ends of the seed lumen 198 and the fluid return lumen. The tip 208 is approximately one centimeter long and is made of polyethylene (preferably ethylene vinyl acetate). The guide wire lumen 200 extends through the tip 208 and is lined with a sleeve 220 of high density/low density polyethylene. This sleeve 220 is made of a material that is of a higher durometer than the tip 208 to resist the guidewire from tearing the tip 208 as the catheter 14 is delivered over a guidewire.

Radiopaque marker bands 222 made from platinum (90%)-iridium (10%) are located at the distal end of the catheter 14 to assist in proper placement of both the catheter 14 and the treating elements. The marker bands 222 are secured to and flush with the exterior of the catheter 14. Alternatively, radiopaque markers may consist of radiopaque ink or tiny radiopaque particles printed or blasted onto the exterior of the catheter 14. In addition, the intraluminal connector 204 at the distal end of the catheter 14 may be made of platinum/iridium so as to be visible under fluoroscopy and possibly eliminate the need for the distal marker band 222. The proximal portion of the catheter may also have a depth marker 224 to indicate when the catheter 14 is near the end of the guide wire so that the fluoroscopy can be turned on just prior to the delivery of radiation.

Strain relief tubing 226 is placed over the proximal end of the catheter 14 and extends distally a short distance from the distal end of the connector where it is secured. The strain relief tubing 226 adds rigidity for protection from kinks or other damage to the catheter 14, and also adds protection from the radioactive treating elements as they are transferred into and out of the catheter 14.

Another embodiment of a rapid exchange delivery catheter that connects to the transfer device is identical to that shown in FIGS. 17 and 20, except that the catheter has no stiffening lumen or stiffening wire and the guidewire lumen extends from a distal tip opening to a guidewire exit port at a location proximal the intraluminal connector. The catheter comprises two lumens, a seed lumen and a fluid return lumen, extending along the length of the catheter between the catheter's proximal end and locations proximal that of the catheter tip. The distal guidewire lumen extends from a distal opening in the guidewire lumen tip to an opening in the sidewall of the catheter at a location proximal that of the fluid return lumen or the intraluminal connector. The guidewire lumen is short preferably 5 cm or less.

The transfer device 12 of the present invention can also be coupled with any of the catheters described in the co-pending application, Ser. No. 08/628,231, filed Apr. 4, 1996, now U.S. Pat. No. 5,899,822 and Ser. No. 08/936,058, filed Sep. 23, 1997, now U.S. Pat. No. 6,013,020.

The treatment elements are preferably radioactive sources as described within application Ser. No. 08/628,231, filed Apr. 4, 1996 now U.S. Pat. No. 5,899,822. The treatment elements consist of twelve radioactive cylinders in series and two marker seeds, one at each end of the radioactive train. The marker seeds are used to properly position the treatment elements at the treatment site and are preferably gold or gold plated, since gold is visible under fluoroscopy, which is used to monitor the radiation delivery. To decrease the source train delivery time to and retrieval time from the distal end of the catheter, the ends of the marker seeds may be slotted or marker seeds can be of gold tubing filled with epoxy. Most preferably, the distal end of the distal marker seed is slotted to prevent it from blocking the opening to the intraluminal connector. The proximal end of the proximal marker seed is also slotted.

In addition to the radiation doses described in the above referenced application Ser. No. 08/628,231, now U.S. Pat. No. 5,899,822 a therapeutic radiation dose of 14 Gy at 2 mm in vessels of approximately 2.7 to approximately 3.35 mm in diameter or of 18 Gy at 2 mm in vessels of approximately 3.35 to approximately 4.0 mm in diameter may be administered to the patient. The mean radioactivity per radioactive source train should be sufficient to deliver approximately 0.080 gray per second at 2 mm from the center line of the source train.

At specific times during the radiation therapy procedure, it may be necessary or desirable to determine the position of the treating element sand marker seeds with respect to the quartz sleeve 36 in the transfer device 12. For example, the user may need to verify that all twelve treating elements and two marker seeds are present within the quartz sleeve 36 before delivery of the elements to the distal end of the catheter 14, and for safety reasons must be sure that all of the treating elements and marker seeds are within the quartz sleeve 36 prior to closing the gate 120 and disconnecting the catheter 14 from the transfer device 12.

To determine whether or not all of the treatment elements are within the quartz sleeve 36, an electronic detection system (shown in FIGS. 27–34), which measures the presence or non-presence of the distal gold marker seed at a single position within the quartz lumen 118, is included in the transfer device 12. This electronic detection system functions similarly to the detection system described in Ser. No. 08/936,058, filed Sep. 23, 1997, now U.S. Pat. No. 6,013,020, to determine and indicate whether or not the treatment elements are within the quartz sleeve 36. However, the means employed by the electronic detection to achieve the end result is altered significantly to produce a simpler, more efficient system that uses less battery power, and provide a more accurate reading of the location of the treatment elements and marker seeds.

The system calorimetrically detects a gold marker by shining light of different wavelengths onto the small area where the gold marker should reside within the quartz housing 36 and then measuring the reflectivity. Based on the way reflectivity varies with wavelength, the system determines whether a gold object (gold marker) or non-gold object (stainless steel seed, background, or saline filled quartz lumen) is occupying the area. If a gold marker seed is detected, it would be reasonable to conclude with a safe degree of certainty that it is the distal marker seed and that all of the elements proximal to the distal marker seed are also within the quartz housing 36. To increase the degree of certainty that all seeds are within the quartz housing 36, the electronic sensor can be made to determine whether both marker seeds are properly positioned within the quartz housing 36. However, this requires more space within the transfer device for housing additional electronic and optical components.

In practice, photosensors are not equally sensitive to blue and red light and the intensity of one or the other must be adjusted by a fixed compensation factor to achieve the condition where the photosensor electrical output is the same for both colors. This technique is well known to those well versed to opto-electronics, and for the purposes of the rest of this description, where it is stated that the red and blue intensities are equal, it is understood that the intensities are equal as measured by the output of the photosensor.

In addition to detecting the absence or presence of a gold marker at a specific position in the quartz sleeve lumen 118, the electronics wait in a low power state for the power button 22 to be pressed, flash all indicator Light-Emitting Diodes (LEDs) 28a–d, 30, 32a–b on and off for about 4.7 seconds after the power button 22 has been pressed to indicate that the LEDs and batteries 228 are functional, detect the presence or absence of a gold marker as view by an optical sensor, indicate whether a gold marker is detected by illuminating one of two seed sensing indicator LEDs 32a and 32b, and finally automatically return to the low power state after five minutes has elapsed to conserve the battery power, or restart the five minute timing period if the button 22 is pressed again during those five minutes.

The electronic system is powered by two 6 v battery packs 228 which contain two 3 v lithium cells used in series to produce +6 v in each pack. The output is also inverted to produce a −6 v supply required by the electronic circuitry. Examples of such batteries include Sanyo CR-P2, Panasonic CR-P2, and Duracell DL223A batteries. For safety precautions, a fuse is in series with the battery. When necessary, the lower shell half 18 of the transfer device can be removed to replace the battery packs 228.

Figure 23:
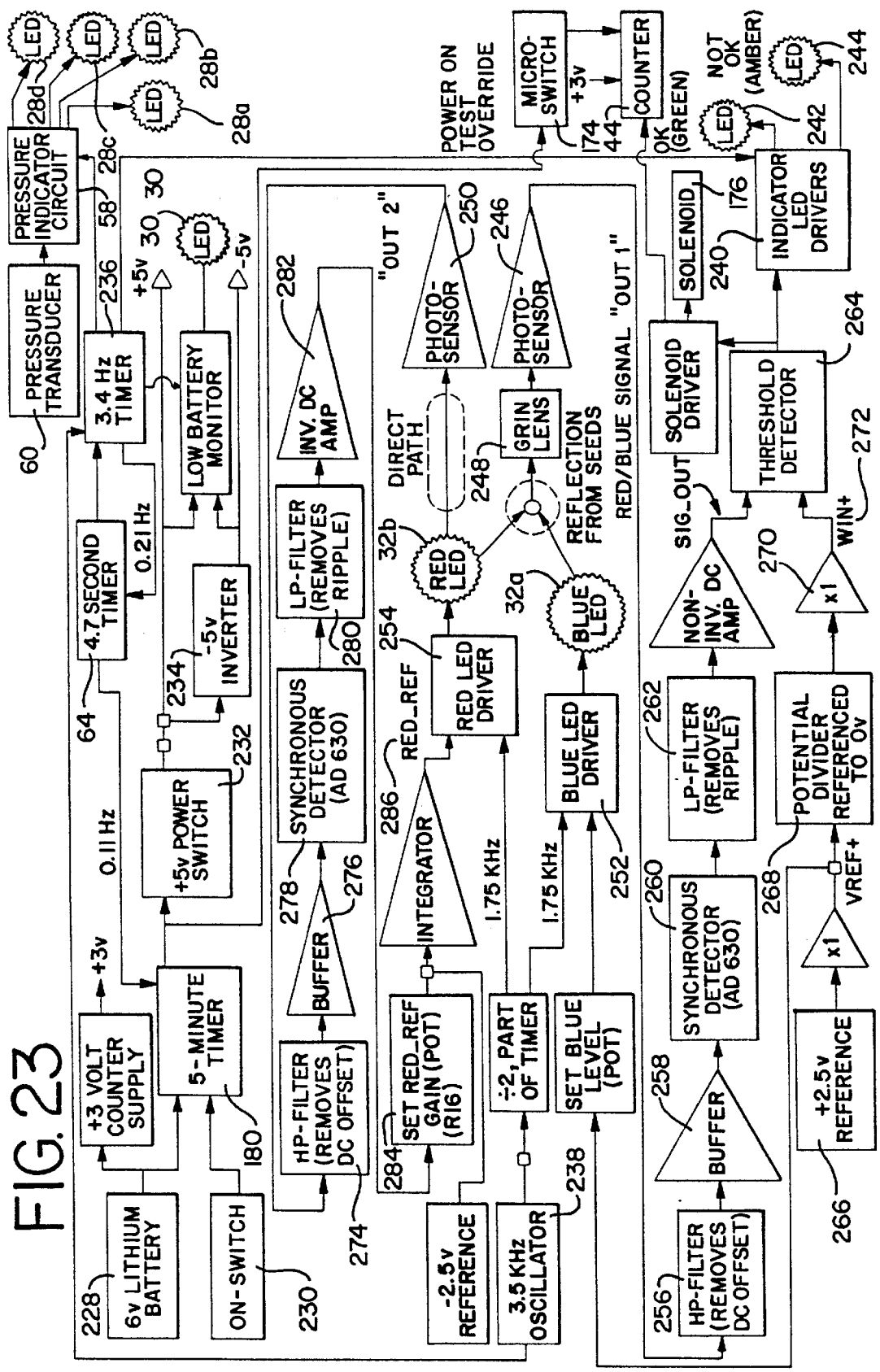
FIG. 23 is a logic diagram for a treating element verification system used in the transfer device of FIG. 1.

The power supply is controlled by a sleep circuit. Applying power turns the sleep circuit off, which in turn shuts down the power supply so that it draws only enough power to keep the system alive. With reference to FIG. 23, the on-switch 230 is a single pole single throw (SPST) push button switch 22. When the switch 230 is closed by momentarily pressing the button 22 from the exterior of the transfer device 12, the sleep circuit is awakened and turns on the power supplies 232,234, one generating +5 v and the other generating −5 v. The power generated is first applied by starting the countdown of an internal timer 180 (a counter driven by 27.3 Hz set for five minutes). At the end of five minutes, the power supplies 232,234 are turned off and the sleep circuit becomes inactive until the next time the switch 230 is closed. If the button 22 is pressed during the five minute timing period, the timing period is reset allowing the power to stay on longer than five minutes. The internal timer 180 can be set for one of several durations in the existing design. Each time the five minute timer 180 starts a 4.7 second test phase, timer 64 also begins and enables a 3.4 Hz timer 236, which is derived from a 3.5 kHz oscillator 238. The 3.4 Hz timer 236 and the 4.7 second timer 64 are applied to the seed indicator LED drivers 240 to flash the two seed indicator LEDs 32a and 32b (one is green and the other is amber) on and off simultaneously at 3.4 Hz for 4.7 seconds. The timers are also applied to flash on and off the low battery indicator LED 30 and pressure indicator LEDs 28a–d. This action informs the user that the batteries 228 and seed indicator LEDs 32a and 32b are in working order. After the 4.7 second test phase of timer 64, the system goes into its normal detection mode.

The detection mode uses the optical properties of stainless steel (the material encapsulating the radioactive isotope) and gold (the material or plated material of the marker seeds), and the resulting different reflectivities of red and blue light on each of stainless steel and gold. The optics of the system include a blue LED 242 employing Gallium Indium Nitride (GaInN), a red LED 244 employing Gallium Phosphide (GaP), a photosensor 246 including a photo diode and integrated amplifier, a GRIN (Gradient Index) lens 248, and a second photosensor 250, which are all housed within the block member 108 that houses the quartz sleeve 36. The first photosensor 246 is perpendicularly oriented with respect to the quartz sleeve 36, and the blue and red LEDs 242,244 are oriented at an angle on either side of the first photosensor 250. Channels within the body direct light from the LEDs 242,244 to a targeted location along the quartz sleeve 36 and also direct the reflected light back to the first photosensor 246. The GRIN lens 248, positioned between the quartz sleeve 36 and the first photosensor 246, focuses on the quartz lumen 118 at the site where the distal gold marker should reside when all of the treating elements are within the quartz sleeve 36. The GRIN lens 248 then produces an image that becomes roughly focused onto the surface of the photodiode. The axes of the GRIN lens, the red and blue LEDs, and the first photosensor must all intersect at or very near the same point along the axis of the quartz housing 36 to reliably determine the presence or non-presence of a gold marker seed.

The blue and red LEDs 242,246 used in this system supply blue and red light at peak wavelengths of 470 nanometers (nm) and 88 nanometers (nm) respectively. At 470 nm, stainless steel has more than 90% reflectance, and gold has about 35% reflectance; at 88 nm both stainless steel and gold have more than 90% reflectance. This means that stainless steel reflects blue and red light about equally well, and gold reflects well in the red light but poorly in the blue light (gold actually absorbs the blue light). Therefore, the measurement of the blue/red ratio of reflected light can unambiguously determine whether or not a gold colored object, in this case a gold marker, is in the photosensor's field of view.

The frequency of an analog clock oscillator 238 which oscillates at 3.5 kHz is divided by two to create two signals, each having a frequency of 1.75 kHz, to flash the blue and red LEDs 242,244 in turn (180 degrees out of phase). One of the two signals is applied to the blue LED driver 252 and the other is applied to the red LED driver 254 so that each LED 242,244 is driven at approximately 1.75 kHz. Therefore, the on time and the off time of the blue and red LEDs 242,244 are equal as they take turns flashing on and off. The flashes of blue and red light travel from the LEDs 242,244, through channels within the block member 108, and through the quartz sleeve 36 to the targeted location where the distal gold marker should be if all of the seeds are within the quartz lumen 118. If a stainless steel seed or fluid is occupying the targeted location, then both the red and blue light are reflected equally well (approximately 96%). If nothing fills the quartz lumen 118 at the targeted location, then the background, as long as it is untinted, also reflects both blue and red light similarly to that of stainless steel. If a gold marker seed is within the targeted location, then the red light is reflected but much of the blue light is absorbed. A first photosensor 246, consisting of a photo diode and an integrated amplifier, is optically coupled to the targeted location within the quartz 36 by the GRIN lens 248 so that the photosensor 246 can measure the reflectivity in each the blue and red light. From the measured ref lectivity's, the blue/red ratio of reflected light is used to determine the presence or absence of a gold marker.

The viewing window 34 along the top 16 of the transfer device 12 allows ambient light to also be reflected off of the object within the field of view of the photosensor 246. The photosensor 246 will detect the ambient light in addition to the red and blue light. The signal of the ambient light superimposed on the signal of each the blue and red LEDs 242,244 may affect the output of the photosensor 246. The photosensor 246 must be operational with light coming in through the transparent viewing window 34. Therefore, the signals due to ambient sources must be removed from the system. This is done by using in series a high-pass filter 256, a buffer 258, a synchronous detector 260 and a low pass filter 262. The high-pass filter removes all DC (direct current) light signals (e.g. daylight or flashlight), and the buffer helps the synchronous detector to reduce background noise by providing a low impedance drive. The synchronous detector is a circuit which is synchronized with the blue and red LED pulses. The synchronous detector processes the blue and red signals using the same 1.75 kHz oscillator used to drive the blue LED 242 and removes all signals except for those attributable to the blue and red LEDs 242,244 and converts the resulting AC signal to a DC signal. The amplitude of each pulse corresponds to how much light is being reflected from the targeted location and the DC voltage is inversely proportional to the blue/red ratio of reflected light. In the case of gold being present at the targeted location, the DC voltage output is nominally zero. In the case of any other color present at the targeted location, the output is a non-null voltage. The last step in filtering out signals from ambient light is using a low pass filter to remove the ripple on the DC signal exiting the synchronous detector.

The system is designed to produce a nominally null voltage with the detection of gold (and a positive non-zero voltage with the detection of stainless steel or background) because a null signal is unaffected by any gains encountered along the signal path (zero times any magnitude is always zero). Thus, the null signal is much less likely to go outside the tolerance window created around the reference voltage to be detected (null). Because the null signal is less affected by variations within the system, such as mechanical tolerances and temperature changes, it is more reliable than a non-null voltage. After setting the red LED, the only adjustment needed for making the output voltage zero when a gold marker occupies the targeted location is adjusting the intensity of the blue LED 242. Two signals of the same amplitude produce zero volts AC. Conversely, because gold reflects red and absorbs blue when the blue and red LEDs 242,244 are the same intensity, the photosensor 246 sends out signals of different amplitudes (high signal for blue and low signal for bred) which are converted into a non-null DC voltage. In order for the presence of gold to produce a null, gold, not stainless steel, must produce equal amounts of reflection for both the blue and red light. This is done by increasing the drive of the blue LED 242 while maintaining the drive of the red LED 244 constant so that the blue LED 242 illuminates with greater intensity than the red LED 244. The amount by which the drive must be increased is that with which produces equal amplitudes for both red and blue reflected light. By increasing the intensity of the blue light by a specific percentage, gold now reflects the blue light equally as well as the red in comparison to absorbing the blue when the red and blue LEDs 244,242 have the same drive. Now gold reflects equal amounts of the blue and red light which produces no AC signal from the photosensor 246, thus, creating a null. On the other hand, the reflection of stainless steel is brighter with blue because of the boost given to the blue LED driver 252. Therefore, the blue signal is larger than the red signal and the resulting square wave produces a non-zero DC voltage. To make sure the stainless steel treating elements and the background always produce a non-null output voltage, they should be untinted or tinted blue so as to reflect blue and absorb red, which is the opposite of what gold does.

When the DC signal is at nominally zero volts, the system will indicate the detection of gold. In practice, however, due to certain variations within the system, the DC signal will rarely read as zero volts. A positive threshold detector 264 is included in the system to compare the threshold reference voltage with the filtered and rectified DC signal (a true window detector with both positive and negative thresholds centered around zero is not necessary because signals from the stainless steel seeds, saline, and quartz lumen are found to always be positive). The buffered +2.5 v reference voltage 266 travels through a potential divider 268, followed by a unity gain buffer 270 to generate the threshold reference voltage WIN+ 272. The threshold detector 264 receives the DC signal and determines whether or not it exceeds the positive threshold (for example, +450 millivolts). If the signal does not exceed the threshold, then the threshold detector 264 decides that the signal is consistent with the presence of gold. The threshold can be changed in order to vary the tolerance of the system to errors. After the signal goes through the threshold detector 264, the decoded signal enters the two drivers for the indicator LEDS 32a and 32b. If the decoded signal indicates that gold is present, then the green LED 32a along the top 16 of the transfer device 12 within the light pipe 66 is illuminated, displaying to the user that all of the treating elements are within the quartz housing 36. If the decoded signal indicates that gold is not present, then the amber LED 32b along the top 16 of the transfer device 12 within the light pipe 66 is illuminated, displaying to the user that possibly not all of the treating elements are within the quartz housing 36.

Both the blue and red LEDs 242,244 are temperature sensitive. The red LED output significantly decreases as the temperature rises and significantly increases as the temperature drops. These temperature induced changes in the red LED output will disturb the blue/red ratio of reflected light and may hinder the system's ability to detect the presence of gold. To stabilize the red LED output, a brightness control loop is included to regulate the output and compensate for any temperature effects so as to hold the red LED output constant. The blue LED 242, however, is sufficiently temperature stable over the normal operating temperature range of +10° C. to +35° C.; therefore, no brightness control loop is necessary for the blue LED 242. The red LED brightness control loop incorporates a second photosensor 250. The second photosensor 250 compensates for the temperature induced changes in the LED output by focusing at the tip of the red LED 244 only and measuring how much light it is generating. The second photosensor 250 is positioned at a 900 angle with respect to the longitudinal axis of the red LED 244. The red LED output signal is detected in the same way as the blue/red reflective signal by flowing through a high-pass filter 274, buffer 276, synchronous detector 278 and a low pass filter 280. The outcoming DC signal then passes through the noninverting DC amplifier 282 to set the control loop gain 284. The signal adds either a positive or negative gain to the reference signal (RED REF) 286 that sets the red LED drive range. The adjusted signal entering the red LED driver maintains the red LED output constant even though the actual amount of light for any given current may vary.

A block diagram of the system electronics is shown in FIG. 23. As indicated above, the electronics are used to calorimetrically detect the distal gold marker, to detect low battery power, to control an electro-magnetic locking mechanism, to sense and indicate the system pressure to the user, and to display the number of transfer device uses. All electronic circuitry, except for the pressure sensing circuitry, are on the primary and secondary sides of the main printed circuit board, which can be seen in FIGS. 27 and 28 respectively. For testing procedures the main circuit board may have a test connector which makes accessible signals and voltages within the circuit. The main circuit board is coated or stored within a plastic bag for protection against moisture and mounted on the under side of the chassis within the transfer device. The schematic diagrams of the electronics on the main circuit board are shown in FIGS. 29A–D and 30A–C. The micro printed circuit boards which are mounted on the two photosensors 246 and 250 are shown in FIGS. 31, 32 and there schematic diagrams are shown in FIG. 33. The electrical connections between the different parts of the transfer device are shown in FIG. 34.

As a backup to the electronic source detection system, the window 34 above the quartz housing 36 allows the user of the transfer device 12 to visually detect whether or not all of the treating elements are within the quartz housing 36 by either detecting the presence of each marker seed on either side of the treating elements or by counting the number of treating elements and marker seeds within the quartz housing 36. To assist the user with visual detection, a magnifying lens 288 (shown in FIGS. 2, 5, 9 and 14) is secured to the top portion of the block portion 108 where it is situated directly above the quartz lumen 118. The lens used may magnify in one or two dimensions and may have an order of magnification of 2× or greater. The lens is a cylindrical glass lens of plano-convex form. However, other lenses may be used. Also as a means to assist the user with visual detection of the treatment elements and marker seeds, a scribe line or marking may be inscribed onto the surface of the quartz housing as a visual indication to the user that the distal marker seed, and thus all treating elements, is properly positioned within the quartz housing.

Although the inventions have been described in terms of certain specific embodiments, it is understood that various modifications and changes may be made without departing from these inventions and that reference should be made to the appended claims to determine the proper scope of these inventions.

In which is claimed:

1. In a transfer device useable in a system for intraluminal treatment of a selected site in a body of a patient by at least one treatment element advanced through a lumen in the transfer device into a lumen of a separate catheter by means of pressurized fluid, the transfer device having an actuator assembly moveable between a first position that prevents the treatment element from entering the lumen of the catheter and a second position that permits the treatment element to enter the lumen of the catheter, and an electrically-powered detection system for determining the presence or absence of said at least one treatment element within the transfer device, the improvement comprising:

a mechanical interlock operatively connected to said detection system so that said mechanical interlock prevents movement of the actuator assembly unless either said detection system determines the presence of said at least one treatment element within the transfer device or the electrical power for the detection system is off.

2. The transfer device of claim 1 wherein the mechanical interlock comprises a solenoid having a plunger that moves between an extended position in which it engages the actuator assembly to prevent movement thereof and a retracted position to disengage the actuator assembly.

3. A method for inhibiting stenosis in an area of a vessel having an inside diameter of between approximately 2.7 mm and 3.35 mm with an intraluminal radiation source having a center line comprising providing a radiation dose of 14 Gy to said blood vessel in the area at a distance of 2 mm from the centerline of the intraluminal radiation source.

4. A method of inhibiting restenosis in an area of a vessel having an inside diameter of approximately 3.35 mm to 4.0 mm with an intraluminal radiation source having a centerline comprising providing a radiation dose of 18 Gy to said blood vessel in the area at a distance of 2 mm from the centerline of the intraluminal radiation source.

5. A method for inhibiting restenosis in an area of a vessel comprising providing an intraluminal radiation source having a centerline, the mean radioactivity of said source being sufficient to deliver a radioactive dose of approximately 0.080 Gy/sec at a distance of 2 mm from the centers of the radioactive source.

6. In a transfer device useable in a system for intraluminal treatment of a selected site in a body of a patient by at least one treatment element advanced through a lumen in the transfer device into a lumen of a separate catheter by means of pressurized fluid received through a fluid entry port in the transfer device, the improvement comprising:

a pressure sensor and indicator including a pressure transducer in fluid communication with said fluid entry port, the transducer taking a measurement of the pressure of fluid as it flows through the transfer device, the pressure measurement being converted to a voltage proportional to the pressure, and a visual indicator actuated by the voltage.

7. The transfer device of claim 6 wherein the visual indicator comprises a series of lights, each light in the series being illuminated upon the pressure transducer generating a predetermined threshold voltage corresponding to predetermined threshold pressure.

8. The transfer device of claim 7 wherein the series of lights comprises first, second, third and fourth light emitting diodes, the first light emitting diode being illuminated when the threshold pressure exceeds 6 psi, the second light emitting diode being illuminated when the threshold pressure exceeds 10 psi, the third light emitting diode being illuminated when the threshold pressure exceeds 60 psi, and the fourth light emitting diode being illuminated when the pressure exceeds 80 psi.

9. The transfer device of claim 8 when the first, second and third light emitting diode emit yellow light and the fourth light emitting diode emits red light.

10. In a transfer device useable in a system for intraluminal treatment of a selected site in a body of a patient by at least one treatment element advanced through a lumen in the transfer device into the lumen of a separate catheter by means of pressurized fluid, the transfer device having battery powered mechanisms and displays, the improvement comprising:

a low battery power indicator comprising at least one comparator to compare the battery voltage to a predetermined threshold voltage and a visual display activated by the comparator if the battery voltage is below the predetermined threshold.

11. The transfer device of claim 10 wherein the visual indicator comprises a light that flashes on and off when the battery voltage is below the predetermined threshold.

12. In a transfer device useable in a system for intraluminal treatment of a selected site in a body of a patient by at least one treatment element advanced from the transfer device into a lumen of a catheter by means of pressurized fluid, the transfer device being in communication with a source of pressurized fluid, the improvement comprising:

a pressure relief valve including a housing having an interior fluid passageway along its length, a fluid inlet at a first end of said housing in communication with the source of pressurized fluid, and a fluid outlet at a second end of said housing, a piston received within said fluid passageway of said housing; a spring within said fluid passageway biasing said piston into fluid-tight contact with said fluid inlet, said spring exerting a predetermined force upon said piston so that if the pressurized fluid exerts a force on said piston greater than said predetermined force, the piston moves against the force of the spring to break the fluid-tight contact with said fluid inlet, thus permitting pressurized fluid to flow through said housing and out said fluid outlet.

13. In a transfer device useable in a system for intraluminal treatment of a selected site in a body of a patient by at least one treatment element advanced from a lumen in the transfer device into a lumen of a catheter by means of pressurized fluid, the transfer device having an actuator assembly moveable from a first position that prevents the treatment element from entering the lumen of the catheter and a second position that permits the treatment element to enter the lumen of the catheter, the improvement comprising:

a counter for determining the number of uses of said transfer device including a microswitch electronically coupled to a counter display, the microswitch being positioned in relation to said actuator assembly so that when the actuator assembly is moved from a selected one of said first or second positions to the other of said first or second positions, the microswitch is tripped, and the counter display is increased by one.

* * * * *